US010779899B2

(12) United States Patent
Griffiths et al.

(10) Patent No.: US 10,779,899 B2
(45) Date of Patent: *Sep. 22, 2020

(54) AUTOMATIC PUSH-OUT TO AVOID RANGE OF MOTION LIMITS

(71) Applicant: INTUITIVE SURGICAL OPERATIONS, INC., Sunnyvale, CA (US)

(72) Inventors: Paul G. Griffiths, Santa Clara, CA (US); Paul W. Mohr, Mountain View, CA (US); Brandon D. Itkowitz, San Jose, CA (US); Thomas R. Nixon, San Jose, CA (US); Roman Devengenzo, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 138 days.

This patent is subject to a terminal disclaimer.

(21) Appl. No.: 16/016,436

(22) Filed: Jun. 22, 2018

(65) Prior Publication Data

US 2018/0318023 A1    Nov. 8, 2018

Related U.S. Application Data

(63) Continuation of application No. 15/126,541, filed as application No. PCT/US2015/021074 on Mar. 17, 2015, now Pat. No. 10,028,793.

(Continued)

(51) Int. Cl.
*A61B 34/37*    (2016.01)
*A61B 34/35*    (2016.01)
(Continued)

(52) U.S. Cl.
CPC .............. *A61B 34/35* (2016.02); *A61B 34/30* (2016.02); *A61B 90/50* (2016.02); *B25J 9/0033* (2013.01);
(Continued)

(58) Field of Classification Search
USPC .............................. 700/245–264; 606/1, 130
See application file for complete search history.

(56) References Cited

U.S. PATENT DOCUMENTS 3,893,263 A    7/1975 Jackman et al.
4,604,787 A    8/1986 Sievers, Jr.
(Continued)

FOREIGN PATENT DOCUMENTS

CN    202599962 U    12/2012
JP    S60262201 A    12/1985
(Continued)

OTHER PUBLICATIONS

Extended European Search Report for Application No. 18215877.4, dated Feb. 12, 2019, 10 pages.
(Continued)

*Primary Examiner* — Jonathan L Sample
(74) *Attorney, Agent, or Firm* — Artegis Law Group, LLP

(57) ABSTRACT

Devices, systems, and methods include a teleoperated system including a kinematic structure having a joint, a drive or brake system for controlling the joint, and a computing unit coupled with the drive or brake system. The computing unit is configured to detect that the joint is between a software defined range of motion limit for the joint and a physical range of motion limit for the joint, the software defined range of motion limit being spaced a distance apart from the physical range of motion limit and delay for a duration of time, in response to detecting the joint between the software defined range of motion limit and the physical range of (Continued)

motion limit, applying the drive or brake system to stop motion of the joint.

20 Claims, 22 Drawing Sheets

Related U.S. Application Data

(60) Provisional application No. 61/954,452, filed on Mar. 17, 2014, provisional application No. 62/019,311, filed on Jun. 30, 2014.

(51) Int. Cl.
*A61B 34/30* (2016.01)
*A61B 90/50* (2016.01)
*F16M 13/02* (2006.01)
*B25J 9/00* (2006.01)
*B25J 9/16* (2006.01)
*B25J 19/00* (2006.01)
*A61B 90/00* (2016.01)

(52) U.S. Cl.
CPC ......... *B25J 9/1689* (2013.01); *B25J 19/0004* (2013.01); *F16M 13/022* (2013.01); *A61B 90/03* (2016.02); *A61B 2090/5025* (2016.02)

(56) References Cited

U.S. PATENT DOCUMENTS

| | | | |
|---|---|---|---|
| 4,943,020 A | 7/1990 | Beaucoup | |
| 5,279,309 A | 1/1994 | Taylor et al. | |
| 5,710,870 A * | 1/1998 | Ohm | B25J 3/04 |
| | | | 700/245 |
| 5,784,542 A | 7/1998 | Ohm et al. | |
| 5,923,139 A | 7/1999 | Colgate et al. | |
| 6,120,433 A | 9/2000 | Mizuno et al. | |
| 6,367,757 B1 | 4/2002 | Aramaki | |
| 6,393,340 B2 | 5/2002 | Funda et al. | |
| 6,434,507 B1 | 8/2002 | Clayton et al. | |
| 6,484,993 B2 | 11/2002 | Huffman | |
| 6,493,608 B1 | 12/2002 | Niemeyer | |
| 6,645,196 B1 | 11/2003 | Nixon et al. | |
| 6,714,839 B2 * | 3/2004 | Salisbury, Jr. | B25J 3/00 |
| | | | 318/568.11 |
| 6,788,018 B1 * | 9/2004 | Blumenkranz | B25J 9/0018 |
| | | | 128/DIG. 7 |
| 7,883,458 B2 | 2/2011 | Hamel | |
| 8,191,322 B2 | 6/2012 | Liestenfeltz et al. | |
| 8,357,144 B2 | 1/2013 | Whitman et al. | |
| 8,506,556 B2 | 8/2013 | Schena | |
| 8,541,970 B2 * | 9/2013 | Nowlin | A61B 34/77 |
| | | | 318/568.21 |
| 8,749,190 B2 | 6/2014 | Nowlin et al. | |
| 8,849,457 B2 * | 9/2014 | Jacobsen | A61H 3/008 |
| | | | 623/24 |
| 8,914,150 B2 * | 12/2014 | Moll | A61B 34/30 |
| | | | 700/246 |
| 9,267,639 B2 | 2/2016 | Sweere et al. | |
| 9,358,074 B2 | 6/2016 | Schena et al. | |
| 10,028,793 B2 | 7/2018 | Griffiths et al. | |
| 10,201,393 B2 | 2/2019 | Devengenzo et al. | |
| 10,500,006 B2 | 12/2019 | Devengenzo et al. | |
| 2001/0013764 A1 * | 8/2001 | Blumenkranz | A61B 34/70 |
| | | | 318/568.11 |
| 2002/0032452 A1 | 3/2002 | Tierney et al. | |
| 2002/0045888 A1 * | 4/2002 | Ramans | A61B 34/35 |
| | | | 606/1 |
| 2002/0082612 A1 * | 6/2002 | Moll | G09B 23/285 |
| | | | 606/130 |
| 2003/0023346 A1 * | 1/2003 | Salisbury, Jr. | A61B 34/70 |
| | | | 700/245 |
| 2003/0139753 A1 | 7/2003 | Wang et al. | |
| 2005/0193451 A1 | 9/2005 | Quistgaard et al. | |
| 2006/0106493 A1 | 5/2006 | Niemeyer et al. | |
| 2007/0013336 A1 * | 1/2007 | Nowlin | A61B 34/30 |
| | | | 318/568.21 |
| 2007/0142701 A1 | 6/2007 | Goldberg et al. | |
| 2007/0142825 A1 | 6/2007 | Prisco | |
| 2007/0299427 A1 | 12/2007 | Yeung et al. | |
| 2008/0046122 A1 | 2/2008 | Manzo et al. | |
| 2008/0200794 A1 | 8/2008 | Teichman et al. | |
| 2009/0062813 A1 | 3/2009 | Prisco et al. | |
| 2009/0076368 A1 | 3/2009 | Balas | |
| 2009/0076476 A1 | 3/2009 | Barbagli et al. | |
| 2009/0145241 A1 | 6/2009 | Cowgill | |
| 2009/0163929 A1 | 6/2009 | Yeung et al. | |
| 2009/0245600 A1 * | 10/2009 | Hoffman | H04N 13/156 |
| | | | 382/128 |
| 2009/0248036 A1 * | 10/2009 | Hoffman | A61B 1/045 |
| | | | 606/130 |
| 2009/0275798 A1 * | 11/2009 | Naito | A61B 1/00149 |
| | | | 600/106 |
| 2010/0228264 A1 | 9/2010 | Robinson et al. | |
| 2010/0228588 A1 | 9/2010 | Nielsen et al. | |
| 2010/0274087 A1 | 10/2010 | Diolaiti et al. | |
| 2011/0082452 A1 | 4/2011 | Melsky et al. | |
| 2011/0277236 A1 | 11/2011 | Moriarity et al. | |
| 2011/0295248 A1 | 12/2011 | Wallace et al. | |
| 2011/0319714 A1 | 12/2011 | Roelle et al. | |
| 2011/0319815 A1 | 12/2011 | Roelle et al. | |
| 2012/0224673 A1 | 9/2012 | Barker et al. | |
| 2013/0096574 A1 | 4/2013 | Kang et al. | |
| 2013/0223598 A1 | 8/2013 | Simmons et al. | |
| 2014/0031983 A1 | 1/2014 | Low et al. | |
| 2014/0039517 A1 | 2/2014 | Bowling et al. | |
| 2014/0039681 A1 | 2/2014 | Bowling et al. | |
| 2014/0052153 A1 | 2/2014 | Griffiths et al. | |
| 2014/0052154 A1 * | 2/2014 | Griffiths | B25J 9/1633 |
| | | | 606/130 |
| 2014/0222207 A1 | 8/2014 | Bowling et al. | |
| 2015/0250547 A1 * | 9/2015 | Fukushima | B25J 9/1697 |
| | | | 606/130 |
| 2015/0257840 A1 * | 9/2015 | Mohr | A61B 34/37 |
| | | | 606/130 |
| 2016/0367334 A1 | 12/2016 | Devengenzo et al. | |
| 2017/0080574 A1 * | 3/2017 | Kuroda | H04N 5/2251 |
| 2017/0112580 A1 * | 4/2017 | Griffiths | F16M 13/022 |

FOREIGN PATENT DOCUMENTS

WO WO-2014028699 A1 2/2014
WO WO-2015142786 A1 9/2015

OTHER PUBLICATIONS

International Search Report and Written Opinion for Application No. PCT/US15/20878, dated Jul. 14, 2015, 13 pages.
International Search Report and Written Opinion for Application No. PCT/US15/21047, dated Jun. 8, 2015, 13 pages.
Extended European Search Report for Application No. 15764074.9, dated Oct. 11, 2017, 6 pages.
Extended European Search Report for Application No. 15765708.1, dated Oct. 16, 2017, 8 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP20157530.5 dated Jun. 3, 2020, 6 pages.

* cited by examiner

AUTOMATIC PUSH-OUT TO AVOID RANGE OF MOTION LIMITS

CROSS-REFERENCE TO RELATED APPLICATIONS

This application is a continuation of U.S. patent application Ser. No. 15/126,541 filed Sep. 15, 2016, which is a U.S. National Stage application of PCT/US2015/021047 filed Mar. 17, 2015; which claims priority to U.S. Provisional Patent Application 61/954,452 filed Mar. 17, 2014; and to U.S. Provisional Patent Application 62/019,311 filed Jun. 30, 2014, the disclosures of which are incorporated herein by reference.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and avoid some of the limitations on traditional minimally invasive techniques. (Teleoperated medical devices, such as surgical systems, are sometimes called robotic surgical systems because they incorporate robot technology). In telesurgery, the surgeon uses some form of remote control (e.g., a servomechanism or the like) to manipulate surgical instrument movements, rather than directly holding and moving the instruments by hand. In telesurgery systems, the surgeon can be provided with an image of the surgical site at a surgical workstation. While viewing a two or three dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI® system commercialized by Intuitive Surgical, Inc. of Sunnyvale, Calif.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912; 6,758,843; 6,246,200; and 5,800,423; the full disclosures of which are incorporated herein by reference. These linkages often make use of a parallelogram arrangement to hold an instrument having a shaft. Such a manipulator structure can constrain movement of the instrument so that the instrument pivots about a remote center of manipulation positioned in space along the length of the rigid shaft. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 7,763,015; 6,702,805; 6,676,669; 5,855,583; 5,808,665; 5,445,166; and 5,184,601; the full disclosures of which are incorporated herein by reference.

A variety of structural arrangements can also be used to support and position the robotic surgical manipulator and the surgical instrument at the surgical site during robotic surgery. Supporting linkage mechanisms (e.g., serial kinematic chains of two or more individual links, connected by moveable joints, and the like), sometimes referred to as set-up joints, or set-up joint arms, are often used to position and align each manipulator with the respective incision point in a patient's body. A single linkage may include two or more individual component mechanical joints (or an infinite number, in the case of a continuously flexible structure), but as a whole would be considered a single joint with two or more degrees of freedom corresponding to the individual component joints. The supporting linkage mechanism facilitates the alignment of a surgical manipulator with a desired surgical incision point and targeted anatomy. Exemplary supporting linkage mechanisms are described in U.S. Pat. Nos. 6,246,200; 6,788,018; 7,763,015; and 7,837,674 the full disclosures of which are incorporated herein by reference.

While the new telesurgical systems and devices have proven highly effective and advantageous, still further improvements are desirable. In general, improved minimally invasive robotic surgery systems are desirable. It would be particularly beneficial if these improved technologies enhanced the efficiency and ease of use of robotic surgical systems. For example, it would be particularly beneficial to increase maneuverability, improve space utilization in an operating room, provide a faster and easier set-up, inhibit collisions between robotic devices during use, and/or reduce the mechanical complexity and size of these new surgical systems.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention generally provides improved robotic and/or surgical devices, systems, and methods. Kinematic linkage structures and associated control systems described herein are particularly beneficial in helping system users to arrange the robotic structure in preparation for use, including in preparation for a surgical procedure on a particular patient. Exemplary robotic surgical systems described herein may have one or more kinematic linkage sub-systems that are configured to help align a manipulator structure with the surgical work site. The joints of these set-up systems may be actively driven, passive (so that they are manually articulated and then locked (using drive or brake systems or the like) into the desired configuration while the manipulator is used therapeutically), or a mix of both. Embodiments of the robotic systems described herein may employ a set-up mode in which one or more joints are actively driven in response to manual articulation of one or more other joints of the kinematic chain. In many embodiments, the actively driven joints will move a platform structure that supports multiple manipulators in response to manual movement of one of those manipulators, facilitating and expediting the arrangement of the overall system by moving those multiple manipulators as a unit into an initial orientational and/or positional alignment with the workspace. Input of the manipulator movement and independent positioning of one, some or all of the manipulators supported by the platform can optionally be provided through passive set-up joint systems supporting one, some, or all of the manipulators relative to the platform. Optionally, manual movement of a set-up joint linkage disposed between a manipulator and the platform can result in a movement of the platform, with the platform (and the other manipulators supported thereby) following manual movement of the manipulator with a movement analogous to leading a horse by the nose.

In many embodiments, it may be desirable to keep one, some, or all joints of the kinematic chain off a "hardstop" or physical range of motion limit (ROM limit) associated with the joint or otherwise maintain a desired range of motion for one, some, or all joints of the kinematic chain when exiting the set-up mode. For example, it may be beneficial to keep joints of the kinematic chain off a ROM limit as a safety feature of a surgical system. In a system with redundant degrees of freedom (DOFs), if a relatively more distal joint is at a ROM limit (e.g., fully compressed), and then one or more relatively more proximal joints are moved in a DOF redundant to the distal joint, the arm distal of the distal joint may exert extremely high forces against an object (e.g., operating table or the like) or patient. Accordingly, it may be beneficial to push the joint from a physical ROM limit or to otherwise maintain a desired range of motion of the joint so as to provide a buffering zone between the joint and the physical ROM limit. While drive or brake systems may be actuated to maintain a joint in a resting and/or locked position, there may still be play or limited movement of the joint, for example, if the joint experiences outside forces that exceed the drive or brake forces. Thus the buffering zone may absorb and/or counteract joint motion toward the ROM limit and provide an additional layer of safety measures for the surgical system.

In some embodiments, the push-out feature or buffering zone may be provided as a control algorithm. Physical and/or virtual springs may be installed or provided at the ends of the joint's range of motion. When a user manually pushes the joint into the spring against the physical ROM limit and signals to reengage a drive or brake system associated with the joint, a control unit may delay an application of the joint drive or brake system for at least a delay duration. The delay in the application of the joint or brake system may allow the physical (or virtual) spring to push the joint out a distance before reapplying the joint drive or brake system for fixing the position of the joint.

Accordingly, in a first aspect a method of controlling a surgical system is provided. The system may have a surgical manipulator coupled with a support structure by a set-up linkage. The set-up linkage may include at least one joint having a range of motion between a first physical range of motion limit and a second physical range of motion limit. The set-up linkage may be configured to facilitate an alignment of the surgical manipulator with a desired position and orientation relative to the support structure. The set-up linkage may further include a drive or brake system operatively coupled to the set-up linkage and configured to limit inadvertent movement of the set-up linkage relative to the support structure when applied. For example, the joint may include a motor where current may be run through the motor to counteract manual articulation. Additionally, or alternatively, the joint may include a joint brake for fixing the joint state. The method may include defining a first software range of motion limit spaced a distance apart from the first physical range of motion limit of the joint and a second software range of motion limit spaced a distance apart from the second physical range of motion limit of the joint. The range of motion between the software defined range of motion limit and the associated physical range of motion limit may define a range of motion limit envelope. Optionally, the range of motion limit envelope may act as a buffer zone or push-out zone. The method may further include receiving a first user input for halting a driving or braking by the drive or brake system to allow for manual positioning of the manipulator relative to the support structure through movement of the at least one joint of the set-up linkage. A driving or braking by the drive or brake system may be halted in response to receiving first the user input. A position of the joint within the range of motion of the joint may be detected. For example, in some embodiments, the position may be detected through one or more encoders associated with the joint. The method may further include receiving a second user input for reapplying the driving or braking by the drive or brake system. In response to receiving the second user input, the method may include delaying reapplication of the driving or braking by the drive or brake system of the set-up linkage for at least a threshold duration of time when the joint position is detected to be outside a preferred range of positions defined by the range of motion between the first or second software defined range of motion limits. Put in another way, when the system detects motion between the first software defined range of motion limit and the first physical range of motion limit or between the second software defined range of motion limit and the second physical range of motion limit, the system may delay reapplication of the driving or braking by the drive or brake system of the set-up linkage for a duration of time.

The joint may be a prismatic joint where the first physical range of motion limit occurs when the prismatic joint is fully extended and where the second physical range of motion limit occurs when the prismatic joint is fully compressed. The first range of motion limit envelope may be a range of motion of 0.5 inches or less that extends from the first physical range of motion limit to the first software defined range of motion limit and the second range of motion envelope may be a range of motion of 0.5 inches or less that extends from the second physical range of motion limit to the second software defined range of motion limit. The range of motion between the first software defined range of motion limit and the second software defined range of motion limit may define a preferred range of positions for the joint.

The prismatic joint may include one or more springs at the first physical range of motion limit extending within the first range of motion limit envelope to resist movement of the prismatic joint to the fully extended configuration and one or more springs at the second physical range of motion limit extending within the second range of motion limit envelope to resist movement of the prismatic joint to the fully compressed configuration. In some embodiments, the one or more springs may extend from the physical range of motion limit to the associated software defined range of motion limit of the joint when at rest. In further embodiments, the one or more springs may extend from the physical range of motion limit past the associated software defined range of motion limit of the joint when at rest.

In some embodiments, the prismatic joint may be a vertical set-up joint or a horizontal set-up joint. Optionally the joint may be a pivot joint or cylindrical joint.

Joint position may be detected within the first or second range of motion limit envelopes by detecting a compression of the one or more springs at the first physical range of motion limit or the second physical range of motion limit. Optionally, while delaying the reapplication of the driving or braking by the drive or brake system of the set-up linkage, the one or more springs at the first or second physical range of motion limit are configured to absorb motion toward the associated physical range of motion limit and/or to passively push the joint back to a position between the first and second software defined range of motion limits. The method may include reinitializing the driving or braking by the drive or brake system of the set-up linkage after the one or more springs passively push the joint back to a position within the range of motion between the first and second software defined range of motion limits.

The method may further include, after delaying reapplication of the driving or braking by the drive or brake system of the set-up linkage for the threshold duration of time, reinitializing the driving or braking by the drive or brake system of the set-up linkage while the joint is positioned within the first range of motion limit envelope or the second range of motion limit envelope and outputting an error signal in a manner perceptible to an operator. The error signal may be cleared after the joint is moved to a position within a preferred range positions between the first software defined range of motion limit and the second software defined range of motion limit. Thereafter the driving or the braking by the drive or brake system of the set-up linkage may be reapplied with the joint positioned away from the hardstop within the preferred range of positions.

In some embodiments, the drive system may be a motor coupled with a mechanical constant force spring. The method may include driving the motor to increase a spring constant associated with the mechanical constant force spring when detecting the position of the joint within the first range of motion limit envelope or within the second range of motion limit envelope. The method may also include increasing the spring constant of the mechanical constant force spring as the joint nears the first software defined range of motion limit and increasing the spring constant of the mechanical constant force spring as the joint nears the second software defined range of motion limit.

In further embodiments, a teleoperated surgical system may be provided. The system may include a surgical manipulator coupled with a support structure by a set-up linkage. The set-up linkage may include at least one joint having a range of motion between a first physical range of motion limit and a second physical range of motion limit. The set-up linkage may be configured to facilitate an alignment of the surgical manipulator with a desired position and orientation relative to the support structure. The set-up linkage may further include a drive or brake system operatively coupled to the set-up linkage and configured to limit inadvertent movement of the set-up linkage relative to the support structure when applied. The system may also include a switch positioned along the manipulator or set-up linkage and configured for operator actuation of the drive or brake system of the set-up linkage to selectively halt or apply a driving or braking by the drive or brake system to allow for manual positioning of the manipulator relative to the support structure through movement of the at least one joint of the set-up linkage. A computing unit may be coupled with the drive or brake system of the set-up linkage. The computing unit may be configured to detect a position of the joint within the range of motion. The computing unit may identify a first software range of motion limit spaced a distance apart from the first physical range of motion limit of the joint and defining a first range of motion limit envelope between the first software defined range of motion limit and the first physical range of motion limit. The computing unit may further identify a second software range of motion limit spaced a distance apart from the second physical range of motion limit of the joint and defining a second range of motion limit envelope between the second software defined range of motion limit and the second physical range of motion limit. The computing unit may be configured to operate the drive or brake system of the set-up linkage to increase a resistance against manual movement of the joint toward the first software defined range of motion limit and the second software defined range of motion limit. When the computing unit detects the joint positioned within the first or second range of motion limit envelopes, the computing unit may be configured to delay reapplication of the driving or braking by the drive or brake system of the set-up linkage for at least a threshold duration of time.

The joint may be a prismatic joint (e.g., vertical or horizontal joint) where the first physical range of motion limit occurs when the prismatic joint is fully extended and where the second physical range of motion limit occurs when the prismatic joint is fully compressed. The first range of motion limit envelope may be a range of motion of 1 inch or less (e.g., 0.5 inches or less, 0.25 inches or less, or the like) between the first software defined range of motion limit and the first physical range of motion limit and the second range of motion limit envelope may be a range of motion of 1 inch or less (e.g., 0.5 inches or less, 0.25 inches or less, or the like) between the second software defined range of motion limit and the second physical range of motion limit.

The prismatic joint may include one or more springs at the first physical range of motion limit extending within the first range of motion limit envelope to resist movement of the prismatic joint to the fully extended configuration. The prismatic joint may further include one or more springs at the second physical range of motion limit extending within the second range of motion limit envelope to resist movement of the prismatic joint to the fully compressed configuration.

The one or more springs at the first physical range of motion limit and the one or more springs at the second physical range of motion limit may be configured to yield 2 to 6 mm when compressed (e.g., 3 to 3.5 mm).

Bumpers may be positioned at the first physical range of motion limit that provide 0.5 to 3 mm (e.g., 1 to 1.5 mm) of material deformation when compressed and bumpers may also be positioned at the second physical range of motion limit to provide 0.5 to 3 mm (e.g., 1 to 1.5 mm) of material deformation when compressed.

The computing unit may be configured to detect joint position within the first or second range of motion limit envelopes by detecting a compression of the one or more springs at the first physical range of motion limit or the second physical range of motion limit. The one or more springs at the first physical range of motion limit may be configured to passively push the joint back to a position between the first and second software defined range of motion limits while the computing unit delays reapplication of the driving or braking by the drive or brake system of the set-up linkage. The computing unit may reinitializes the driving or braking by the drive or brake system of the set-up linkage after the one or more springs passively push the joint back to a position within the range of motion between the first and second software defined range of motion limits. The threshold duration of time may be 3 to 8 seconds (e.g., 4-5 seconds).

After the computing unit delays reapplication of the driving or braking by the drive or brake system of the set-up linkage for the threshold duration of time, the computing unit may allow for reapplication of the driving or braking by the drive or brake system of the set-up linkage while the joint is positioned within the first range of motion limit envelope or within the second range of motion limit envelope. The computing unit may then output an error signal in a manner perceptible to an operator when the driving or braking of the drive or brake system of the set-up linkage is reapplied with the joint positioned within the first range of motion limit envelope or within the second range of motion limit envelope.

The computing unit may clear the error signal after the joint is moved to a position within the range of motion between the first software defined range of motion limit and the second software defined range of motion limit and may allow for the reapplication of the driving or the braking by the drive or brake system of the set-up linkage with the joint positioned between the first and second software defined range of motion limits.

In some embodiments, the drive system may include a motor coupled with a mechanical constant force spring. The computing unit may be coupled with the motor and drive the motor to increase a spring constant associated with the mechanical constant force spring when the computing unit detects the position of the joint within the first range of motion envelope and increases the spring constant associated with the mechanical constant force spring when the computing unit detects the position of the joint within the second range of motion limit envelope. The computing unit may also be configured to gradually increase the spring constant of the mechanical constant force spring as the joint nears the first software defined range of motion limit or the second software defined range of motion limit.

In further embodiments, a medical device may be provided. The medical device may include a manipulator coupled with a support structure by a set-up linkage. The set-up linkage may include at least one joint and may be configured to facilitate an alignment of the manipulator with a desired position and orientation relative to the support structure. The set-up linkage including a drive or brake system operatively coupled to the set-up linkage and configured to limit inadvertent movement of the set-up linkage relative to the support structure. The medical device may include an actuatable input positioned along the manipulator or set-up linkage and that is configured for operator actuation of the drive or brake system of the set-up linkage to selectively halt or apply a driving or a braking by the drive or brake system to allow for manual positioning of the manipulator relative to the support structure through movement of the at least one joint of the set-up linkage. A computing unit may be provided that is coupled with the drive or brake system of the set-up linkage. The computing unit may be configured to detect movement of a position of the at least one joint of the set-up linkage to within a first threshold proximity of a first range of motion limit associated with the at least one joint of the set-up linkage. When detecting the position of the at least one joint within the first threshold proximity in response to the manual positioning of the manipulator relative to the support structure, the computing unit may be configured to delay reapplication of the driving or the braking by the drive or brake system of the set-up linkage in response to reapplication signals associated with the actuatable input. The computing unit may be configured to delay reapplication of the driving or the braking for at least a threshold duration of time. The computing unit may be further configured to allow reapplication of the driving or the braking by the drive or brake system of the set-up linkage after detecting movement of the at least one joint outside the first threshold proximity associated with the first range of motion limit of the joint.

The first threshold proximity may be a range of 0.5 inches or less from the range of motion limit. Optionally the first threshold proximity is a range of 0.25 inches or less from the range of motion limit.

The at least one joint may include one or more springs at the first range of motion limit. The computing unit may detect movement of the at least one joint of the set-up linkage within the first threshold proximity of the first range of motion limit associated with the at least one joint of the set-up linkage by detecting a compression of the one or more springs at the first range of motion limit. The one or more springs at the first range of motion limit may be configured to passively push the joint outside the first threshold proximity of the first range of motion limit while the computing unit delays reapplication of the driving or braking by the drive or brake system of the set-up linkage. The computing unit may also reinitialize the driving or braking by the drive or brake system of the set-up linkage after the one or more springs passively push the joint outside the first threshold proximity of the first range of motion limit. Optionally, the threshold duration of time is at least 3 seconds. For example the threshold duration of time may be between 3-10 seconds. After the computing unit delays reapplication of the driving or braking by the drive or brake system of the set-up linkage for the threshold duration of time, the computing unit may be configured to allow for reapplication of the driving or braking by the drive or brake system of the set-up linkage while the joint is positioned within the first threshold proximity of the first range of motion limit and may thereafter output an error signal in a manner perceptible to an operator when the driving or braking of the drive or brake system of the set-up linkage is reapplied while the joint is positioned within the first threshold proximity of the first range of motion limit.

In some embodiments, the computing unit may clear the error signal after the joint is moved outside the first threshold proximity of the first range of motion limit and may then allow for the reapplication of the driving or the braking by the drive or brake system of the set-up linkage with the joint outside the first threshold proximity of the first range of motion limit.

In further embodiments, the at least one joint includes one or more springs at the range of motion limit that compress when the joint is moved within the first threshold proximity of the first range of motion limit. When the driving or braking by the drive or brake system of the set-up linkage is reapplied with the joint positioned within the first threshold proximity of the first range of motion limit, operator actuation of the actuatable input may briefly halt the driving or braking by the drive or brake system and may thereby allow the one or more springs positioned at the first range of motion limit to automatically push the joint out from the first threshold proximity of the first range of motion limit. The computing unit may then automatically reapply the driving or braking by the drive or brake system after the joint is pushed out from the first threshold proximity of the first range of motion limit.

The set-up linkage may include the drive system operatively coupled to the set-up linkage. The computing unit may be configured to drive the drive system to increase a resistance against movement of the joint towards the first range of motion limit when the computing unit detects the position of the at least one joint within the first threshold proximity in response to the manual positioning of the manipulator relative to the support structure. The drive system may include a motor coupled with a mechanical constant force spring. The computing unit may be coupled with the motor and drives the motor to increase a spring constant associated with the mechanical constant force spring when the computing unit detects the position of the at least one joint within the first threshold proximity in response to the manual positioning of the manipulator relative to the support structure. The computing unit may be configured to gradually increase the spring constant of the mechanical constant force spring as the joint nears the first range of motion limit.

The joint may be a prismatic joint configured to adjust a height of the manipulator relative to the support structure. The prismatic joint may be at the first range of motion limit when the prismatic joint is fully extended and may have a second range of motion limit when the prismatic joint is fully compressed. The computing unit may be further configured to detect movement of the position of the prismatic joint of the set-up linkage to a position within a second threshold proximity of the second range of motion limit of the prismatic joint. When detecting a position of the prismatic joint within the second threshold proximity in response to the manual positioning of the manipulator relative to the support structure, the computing unit may be configured to delay reapplication of the driving or the braking by the drive or brake system of the set-up linkage for at least the threshold duration of time. The computing unit may further be configured to allow reapplication of the driving or the braking by the drive or brake system of the set-up linkage after detecting movement of the prismatic joint to a position outside the second threshold proximity associated with the second range of motion limit of the prismatic joint. The prismatic joint may include one or more springs at the first range of motion limit, and one or more springs at the second range of motion limit. The one or more springs may be configured to push the prismatic joint outside of the threshold proximity associated with the respective range of motion limit. The set-up linkage may include a drive system operatively coupled to the set-up linkage. The drive system may be a motor coupled with a mechanical constant force spring. The computing unit is coupled with the motor and drives the motor to increase a spring constant associated with the mechanical constant force spring when the computing unit detects a position of the at least one joint within the second threshold proximity of the second range of motion limit.

In further aspects, a method is provided for controlling a joint of a system. The system may have a surgical manipulator coupled with a support structure by a set-up linkage. The set-up linkage may include the joint and the joint may have a range of motion between a first physical range of motion limit and a second physical range of motion limit. The set-up linkage may be configured to facilitate an alignment of the surgical manipulator with a desired position and orientation relative to the support structure. The set-up linkage may further include a motor coupled with a spring and a brake system operatively coupled to the motor and/or the spring to limit inadvertent movement of the set-up linkage relative to the support structure when applied. The system may further include an input for selectively applying the brake system. The method may include detecting a brake release condition for the movable joint that operatively couples to the spring. The brake release condition may be a detection of the joint position within a range of motion limit envelope associated with a physical range of motion limit of the joint in addition to a brake application during movement of the joint through the range of motion envelope or a signal for brake application by the user input. Thereafter, the method may include releasing the brake configured to resist movement of the joint or delaying a reapplication of the brake and allowing the spring to move the joint or to resist a movement of the joint by an external force.

In some embodiments, the brake release condition may be an actuation of a switch by a user. The brake release condition may be an excessive force applied to the joint. The excessive force applied to the joint may results from movement of a redundant mechanical degree of freedom located proximal to the joint. The spring may be a mechanical spring. The spring may include a motor. Thereafter, the method may include reengaging the brake.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

Figure 1:
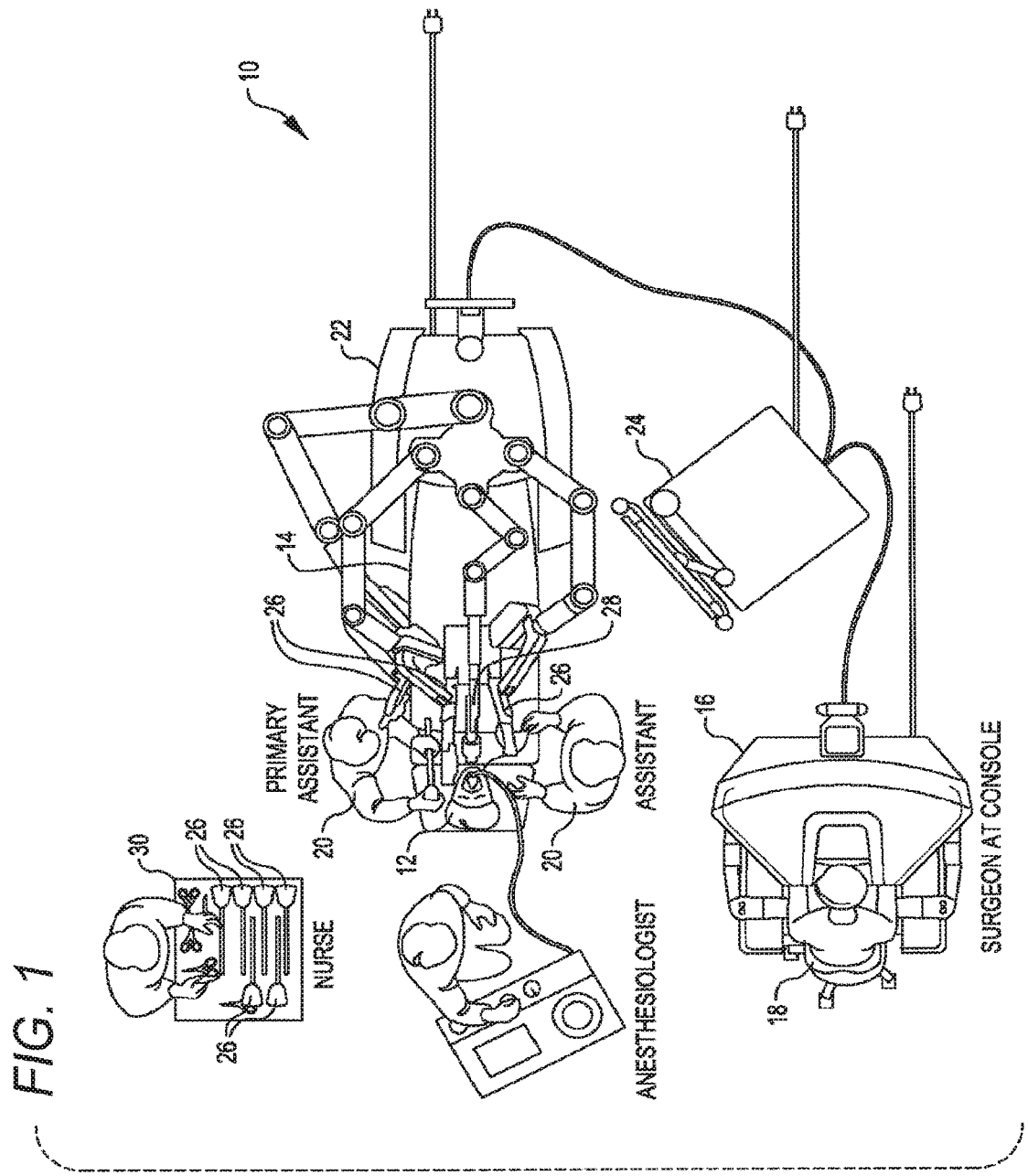
FIG. 1 is a plan view of a minimally invasive robotic surgery system being used to perform a surgery, in accordance with many embodiments.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The kinematic linkage structures and control systems described herein are particularly beneficial in helping system users to arrange the robotic structure of a procedure on a particular patient. Along with actively driven manipulators used to interact with tissues and the like during treatment, robotic surgical systems may have one or more kinematic linkage systems that are configured to support and help align the manipulator structure with the surgical work site. These set-up systems may be actively driven or may be passive, so that they are manually articulated and then locked into the desired configuration while the manipulator is used therapeutically. The passive set-up kinematic systems may have advantages in size, weight, complexity, and cost. Unfortunately, a plurality of manipulators may be used to treat tissues of each patient, the manipulators may each independently benefit from accurate positioning so as to allow the instrument supported by that instrument to have the desired motion throughout the workspace, and minor changes in the relative locations of adjacent manipulators may have significant impact on the interactions between manipulators (with poorly positioned manipulators potentially colliding or having their range and/or ease of motion significantly reduced). Hence, the challenges of quickly arranging the robotic system in preparation for surgery can be significant.

One option is to mount multiple manipulators to a single platform, with the manipulator-supporting platform sometimes being referred to as an orienting platform. The orienting platform can be supported by an actively driven support linkage (sometimes referred to herein as a set-up structure, and typically having a set-up structure linkage, etc.) The system may also provide and control motorized axes of the robotic set-up structure supporting the orienting platform with some kind of joystick or set of buttons that would allow the user to actively drive those axes as desired in an independent fashion. This approach, while useful in some situations, may suffer from some disadvantages. Firstly, users not sufficiently familiar with robotics, kinematics, range of motion limitations and manipulator-to-manipulator collisions may find it difficult to know where to position the orienting platform in order to achieve a good setup. Secondly, the presence of any passive joints within the system means that the positioning of the device involves a combination of manual adjustment (moving the passive degrees of freedom by hand) as well as controlling the active degrees of freedom, which can be a difficult and time-consuming iterative activity.

To maintain the advantages of both manual and actively-driven positioning of the robotic manipulators, embodiments of the robotic systems described herein may employ a set-up mode in which one or more joints are actively driven in response to manual articulation of one or more other joints of the kinematic chain. In many embodiments, the actively driven joints will move a platform-supporting linkage structure that supports multiple manipulators, greatly facilitating the arrangement of the overall system by moving those manipulators as a unit into an initial orientational and/or positional alignment with the workspace. Independent positioning of one, some or all of the manipulators supported by the platform can optionally be provided through passive set-up joint systems supporting one, some, or all of the manipulators relative to the platform.

Minimally Invasive Robotic Surgery

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
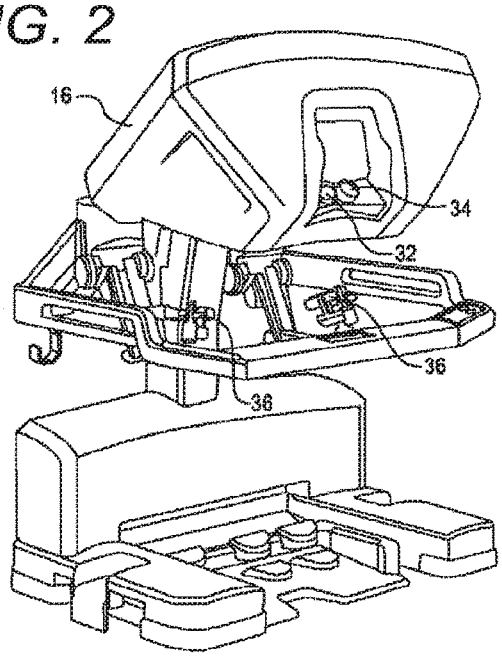
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
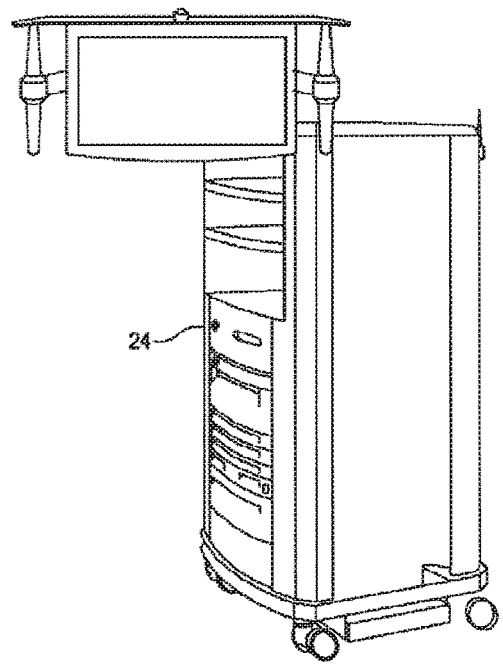
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
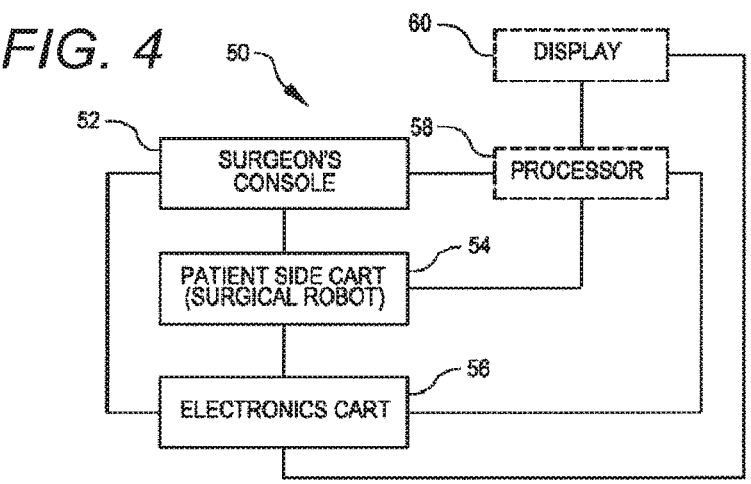
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Processor 58 will typically include a combination of hardware and software, with the software comprising tangible media embodying computer readable code instructions for performing the method steps of the control functionally described herein. The hardware typically includes one or more data processing boards, which may be co-located but will often have components distributed among the robotic structures described herein. The software will often comprise a non-volatile media, and could also comprise a monolithic code but will more typically comprise a number of subroutines, optionally running in any of a wide variety of distributed data processing architectures.

Figure 5A:
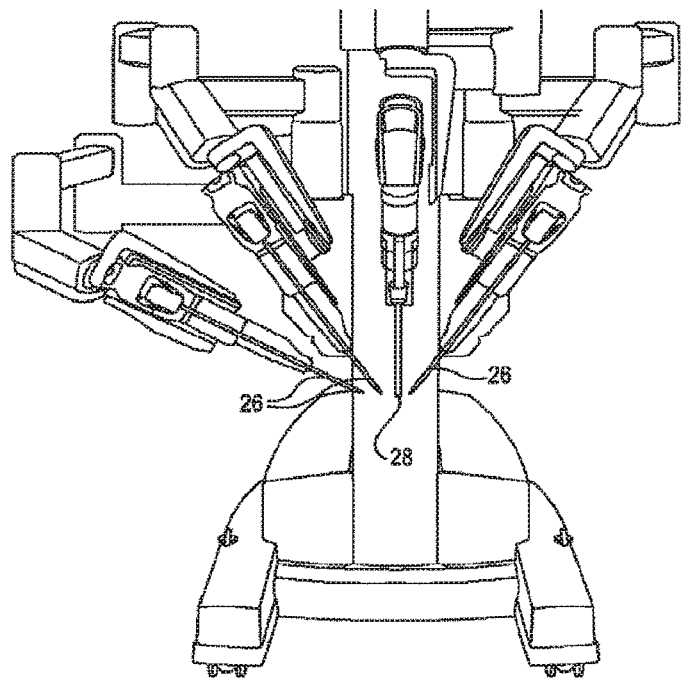
FIG. 5A is a partial view of a patient side cart (surgical robot) of a robotic surgery system, in accordance with many embodiments.
Figure 5B:
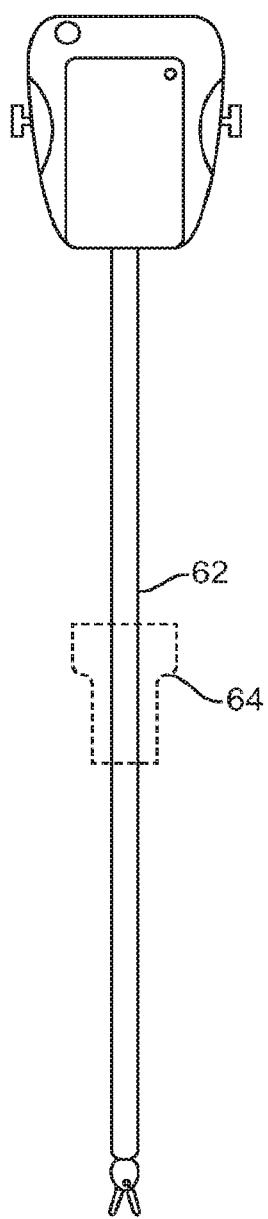
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Surgical tools 26 are inserted into the patient by inserting a tubular cannula 64 through a minimally invasive access aperture such as an incision, natural orifice, percutaneous penetration, or the like. Cannula 64 is mounted to the robotic manipulator arm and the shaft of surgical tool 26 passes through the lumen of the cannula. The manipulator arm may transmit signals indicating that the cannula has been mounted thereon.

Robotic Surgery Systems and Modular Manipulator Supports

Figure 6:
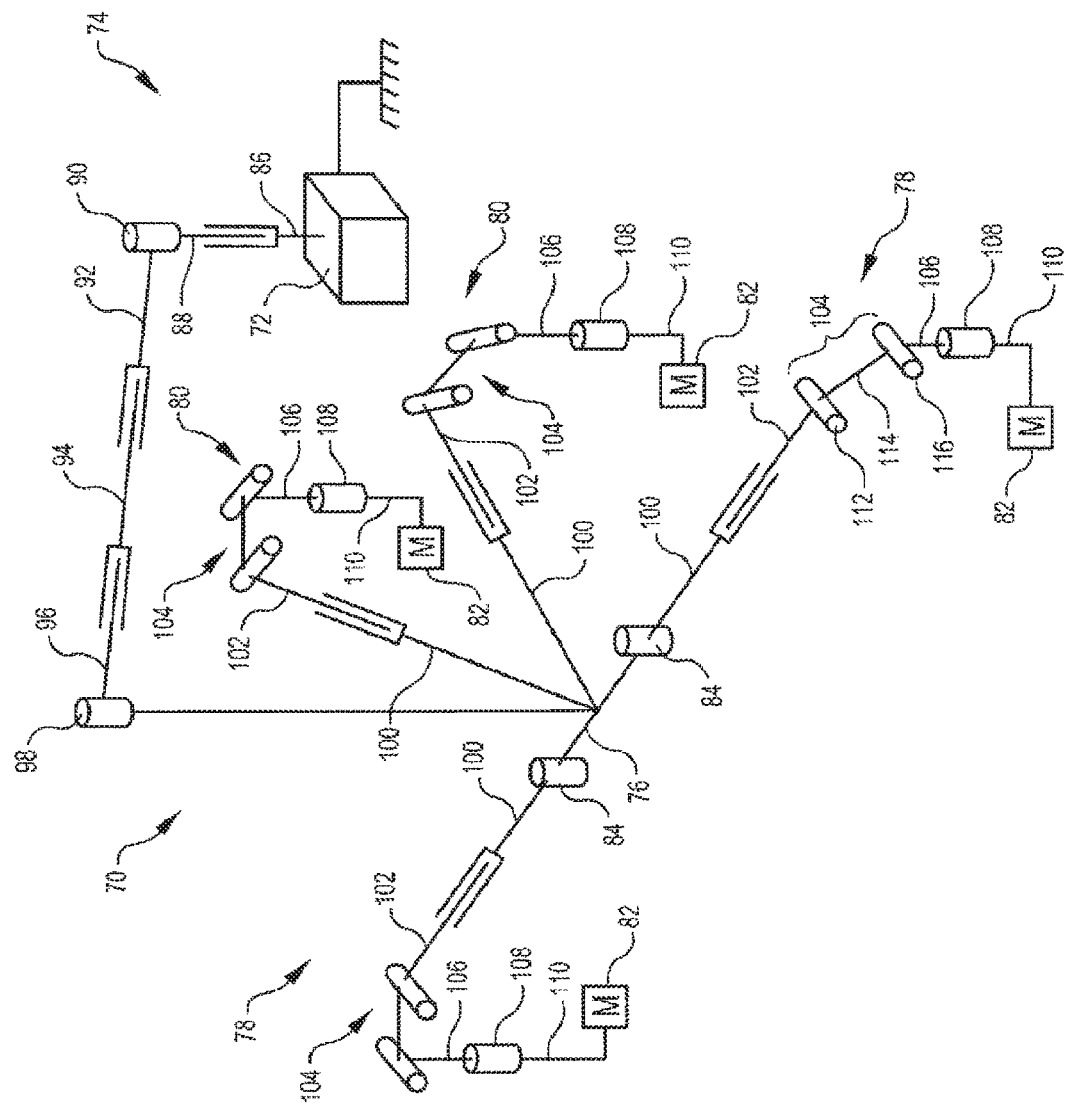
FIG. 6 is a perspective schematic representation of a robotic surgery system, in accordance with many embodiments.

FIG. 6 is a perspective schematic representation of a robotic surgery system 70, in accordance with many embodiments. The surgery system 70 includes a mounting base 72, a support linkage 74, an orienting platform 76, a plurality of outer set-up linkages 78 (two shown), a plurality of inner set-up linkages 80 (two shown), and a plurality of surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 78, 80. Each of the outer set-up linkages 78 is rotationally coupled to and supported by the orienting platform 76 by a first set-up linkage joint 84. Each of the inner set-up linkages 80 is fixedly attached to and supported by the orienting platform 76. The orienting platform 76 is rotationally coupled to and supported by the support linkage 74. And the support linkage 74 is fixedly attached to and supported by the mounting base 72.

In many embodiments, the mounting base 72 is a movable and floor supported, thereby enabling selective repositioning of the overall surgery system 70, for example, within an operating room. The mounting base 72 can include a steerable wheel assembly and/or any other suitable support features that provide for both selective repositioning as well as selectively preventing movement of the mounting base 72 from a selected position. The mounting base 72 can also have other suitable configurations, for example, a ceiling mount, fixed floor/pedestal mount, a wall mount, or an interface configured for being supported by any other suitable mounting surface.

The support linkage 74 is operable to selectively position and/or orient the orienting platform 76 relative to the mounting base 72. The support linkage 74 includes a column base 86, a translatable column member 88, a shoulder joint 90, a boom base member 92, a boom first stage member 94, a boom second stage member 96, and a wrist joint 98. The column base 86 is fixedly attached to the mounting base 72. The translatable column member 88 is slideably coupled to the column base 86 for translation relative to column base 86. In many embodiments, the translatable column member 88 translates relative to the column base 86 along a vertically oriented axis. The boom base member 92 is rotationally coupled to the translatable column member 88 by the shoulder joint 90. The shoulder joint 90 is operable to selectively orient the boom base member 92 in a horizontal plane relative to the translatable column member 88, which has a fixed angular orientation relative to the column base 86 and the mounting base 72. The boom first stage member 94 is selectively translatable relative to the boom base member 92 in a horizontal direction, which in many embodiments is aligned with both the boom base member 92 and the boom first stage member 94. The boom second stage member 96 is likewise selectively translatable relative to the boom first stage member 94 in a horizontal direction, which in many embodiments is aligned with the boom first stage member 94 and the boom second stage member 96. Accordingly, the support linkage 74 is operable to selectively set the distance between the shoulder joint 90 and the distal end of the boom second stage member 96. The wrist joint 98 rotationally couples the distal end of the boom second stage member 96 to the orienting platform 76. The wrist joint 98 is operable to selectively set the angular orientation of the orienting platform 76 relative to the mounting base 72.

Each of the set-up linkages 78, 80 is operable to selectively position and/or orient the associated manipulator 82 relative to the orienting platform 76. Each of the set-up linkages 78, 80 includes a set-up linkage base link 100, a set-up linkage extension link 102, a set-up linkage parallelogram linkage portion 104, a set-up linkage vertical link 106, a second set-up linkage joint 108, and a manipulator support link 110. In each of the set-up linkage base links 100 of the outer set-up linkages 78 can be selectively oriented relative to the orienting platform 76 via the operation of the a first set-up linkage joint 84. In the embodiment shown, each of the set-up linkage base links 100 of the inner set-up linkages 80 is fixedly attached to the orienting platform 76. Each of the inner set-up linkages 80 can also be rotationally attached to the orienting platform 76 similar to the outer set-up linkages via an additional first set-up linkage joints 84. Each of the set-up linkage extension links 102 is translatable relative to the associated set-up linkage base link 100 in a horizontal direction, which in many embodiments is aligned with the associated set-up linkage base link and the set-up linkage extension link 102. Each of the set-up linkage parallelogram linkage portions 104 configured and operable to selectively translate the set-up linkage vertical link 106 in a vertical direction while keeping the set-up linkage vertical link 106 vertically oriented. In example embodiments, each of the set-up linkage parallelogram linkage portions 104 includes a first parallelogram joint 112, a coupling link 114, and a second parallelogram 116. The first parallelogram joint 112 rotationally couples the coupling link 114 to the set-up linkage extension link 102. The second parallelogram joint 116 rotationally couples the set-up linkage vertical link 106 to the coupling link 114. The first parallelogram joint 112 is rotationally tied to the second parallelogram joint 116 such that rotation of the coupling link 114 relative to the set-up linkage extension link 102 is matched by a counteracting rotation of the set-up linkage vertical link 106 relative to the coupling link 114 so as to maintain the set-up linkage vertical link 106 vertically oriented while the set-up linkage vertical link 106 is selectively translated vertically. The second set-up linkage joint 108 is operable to selectively orient the manipulator support link 110 relative to the set-up linkage vertical link 106, thereby selectively orienting the associated attached manipulator 82 relative to the set-up linkage vertical link 106.

Figure 7:
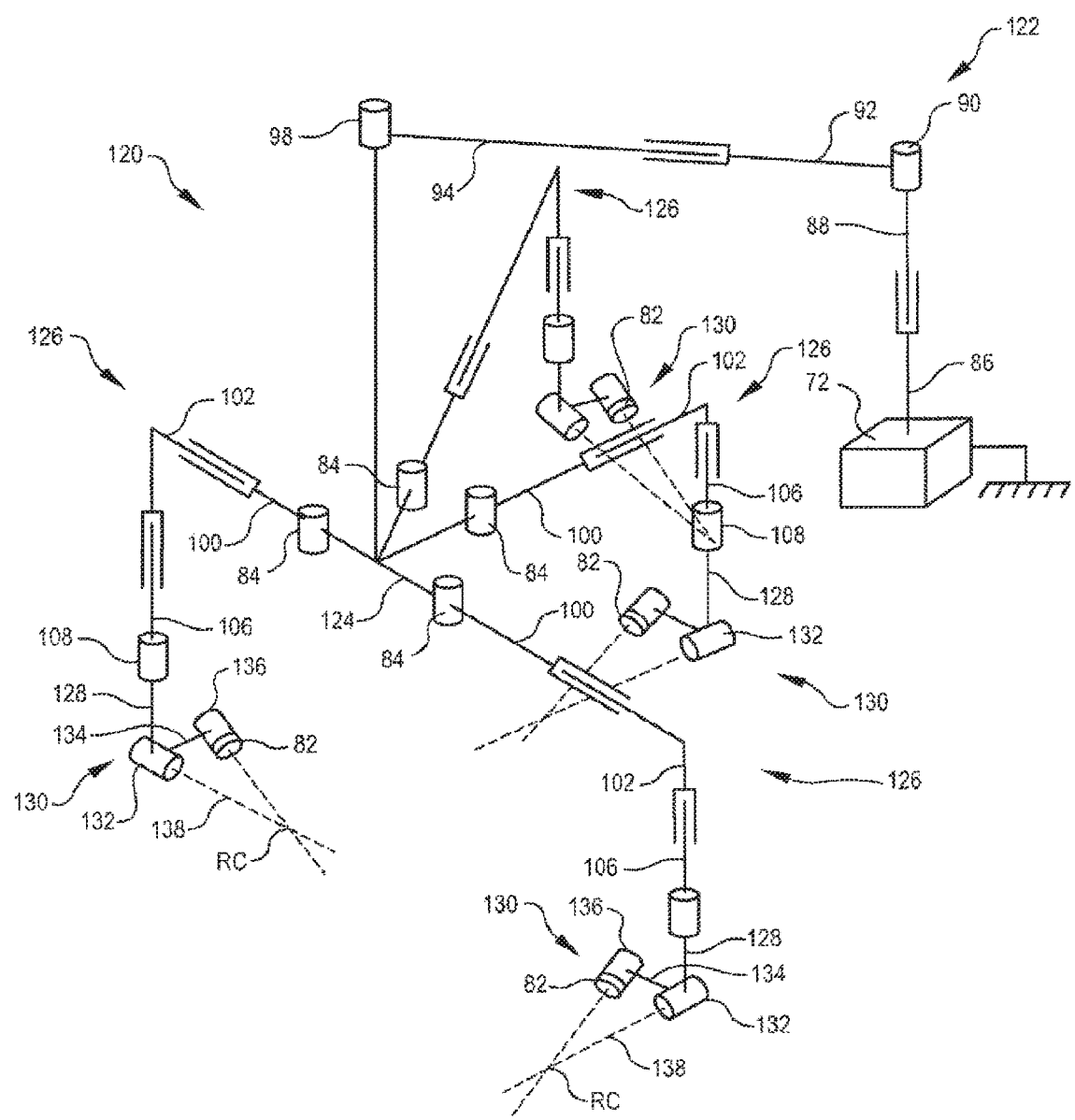
FIG. 7 is a perspective schematic representation of another robotic surgery system, in accordance with many embodiments.

FIG. 7 is a perspective schematic representation of a robotic surgery system 120, in accordance with many embodiments. Because the surgery system 120 includes components similar to components of the surgery system 70 of FIG. 6, the same reference numbers are used for similar components and the corresponding description of the similar components set forth above is applicable to the surgery system 120 and is omitted here to avoid repetition. The surgery system 120 includes the mounting base 72, a support linkage 122, an orienting platform 124, a plurality of set-up linkages 126 (four shown), and a plurality of the surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 126. Each of the set-up linkages 126 is rotationally coupled to and supported by the orienting platform 124 by the first set-up linkage joint 84. The orienting platform 124 is rotationally coupled to and supported by the support linkage 122. And the support linkage 122 is fixedly attached to and supported by the mounting base 72.

The support linkage 122 is operable to selectively position and/or orient the orienting platform 124 relative to the mounting base 72. The support linkage 122 includes the column base 86, the translatable column member 88, the shoulder joint 90, the boom base member 92, the boom first stage member 94, and the wrist joint 98. The support linkage 122 is operable to selectively set the distance between the shoulder joint 90 and the distal end of the boom first stage member 94. The wrist joint 98 rotationally couples the distal end of the boom first stage member 94 to the orienting platform 124. The wrist joint 98 is operable to selectively set the angular orientation of the orienting platform 124 relative to the mounting base 72.

Each of the set-up linkages 126 is operable to selectively position and/or orient the associated manipulator 82 relative to the orienting platform 124. Each of the set-up linkages 126 includes the set-up linkage base link 100, the set-up linkage extension link 102, the set-up linkage vertical link 106, the second set-up linkage joint 108, a tornado mechanism support link 128, and a tornado mechanism 130. Each of the set-up linkage base links 100 of the set-up linkages 126 can be selectively oriented relative to the orienting platform 124 via the operation of the associated first set-up linkage joint 84. Each of the set-up linkage vertical links 106 is selectively translatable in a vertical direction relative to the associated set-up linkage extension link 102. The second set-up linkage joint 108 is operable to selectively orient the tornado mechanism support link 128 relative to the set-up linkage vertical link 106

Each of the tornado mechanisms 130 includes a tornado joint 132, a coupling link 134, and a manipulator support 136. The coupling link 134 fixedly couples the manipulator support 136 to the tornado joint 132. The tornado joint 130 is operable to rotate the manipulator support 136 relative to the tornado mechanism support link 128 around a tornado axis 136. The tornado mechanism 128 is configured to position and orient the manipulator support 134 such that the remote center of manipulation (RC) of the manipulator 82 is intersected by the tornado axis 136. Accordingly, operation of the tornado joint 132 can be used to reorient the associated manipulator 82 relative to the patient without moving the associated remote center of manipulation (RC) relative to the patient.

Figure 8:
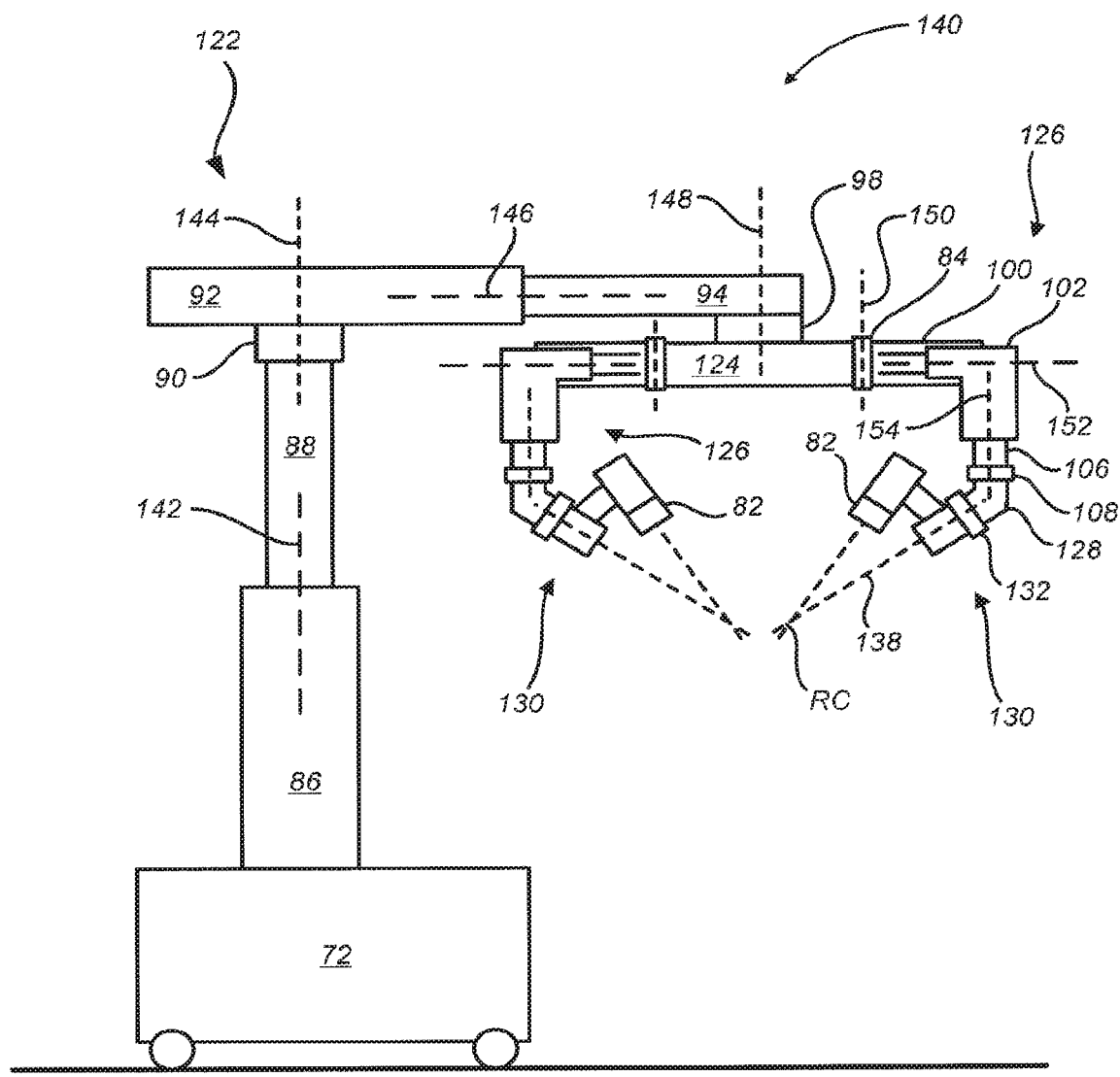
FIG. 8 shows a robotic surgery system, in accordance with many embodiments, in conformance with the schematic representation of FIG. 7.

FIG. 8 is a simplified representation of a robotic surgery system 140, in accordance with many embodiments, in conformance with the schematic representation of the robotic surgery system 120 of FIG. 7. Because the surgery system 140 conforms to the robotic surgery system 120 of FIG. 7, the same reference numbers are used for analogous components and the corresponding description of the analogous components set forth above is applicable to the surgery system 140 and is omitted here to avoid repetition.

The support linkage 122 is configured to selectively position and orient the orienting platform 124 relative to the mounting base 72 via relative movement between links of the support linkage 122 along multiple set-up structure axes. The translatable column member 88 is selectively repositionable relative to the column base 86 along a first set-up structure (SUS) axis 142, which is vertically oriented in many embodiments. The shoulder joint 90 is operable to selectively orient the boom base member 92 relative to the translatable column member 88 around a second SUS axis 144, which is vertically oriented in many embodiments. The boom first stage member 94 is selectively repositionable relative to the boom base member 92 along a third SUS axis 146, which is horizontally oriented in many embodiments. And the wrist joint 98 is operable to selectively orient the orienting platform 124 relative to the boom first stage member 94 around a fourth SUS axis 148, which is vertically oriented in many embodiments.

Each of the set-up linkages 126 is configured to selectively position and orient the associated manipulator 82 relative to the orienting platform 124 via relative movement between links of the set-up linkage 126 along multiple set-up joint (SUJ) axes. Each of the first set-up linkage joint 84 is operable to selectively orient the associated set-up linkage base link 100 relative to the orienting platform 124 around a first SUJ axis 150, which in many embodiments is vertically oriented. Each of the set-up linkage extension links 102 can be selectively repositioned relative to the associated set-up linkage base link 10 along a second SUJ axis 152, which is horizontally oriented in many embodiments. Each of the set-up linkage vertical links 106 can be selectively repositioned relative to the associated set-up linkage extension link 102 along a third SUJ axis 154, which is vertically oriented in many embodiments. Each of the second set-up linkage joints 108 is operable to selectively orient the tornado mechanism support link 128 relative to the set-up linkage vertical link 106 around the third SUJ axis 154. Each of the tornado joints 132 is operable to rotate the associated manipulator 82 around the associated tornado axis 138.

Figure 9:
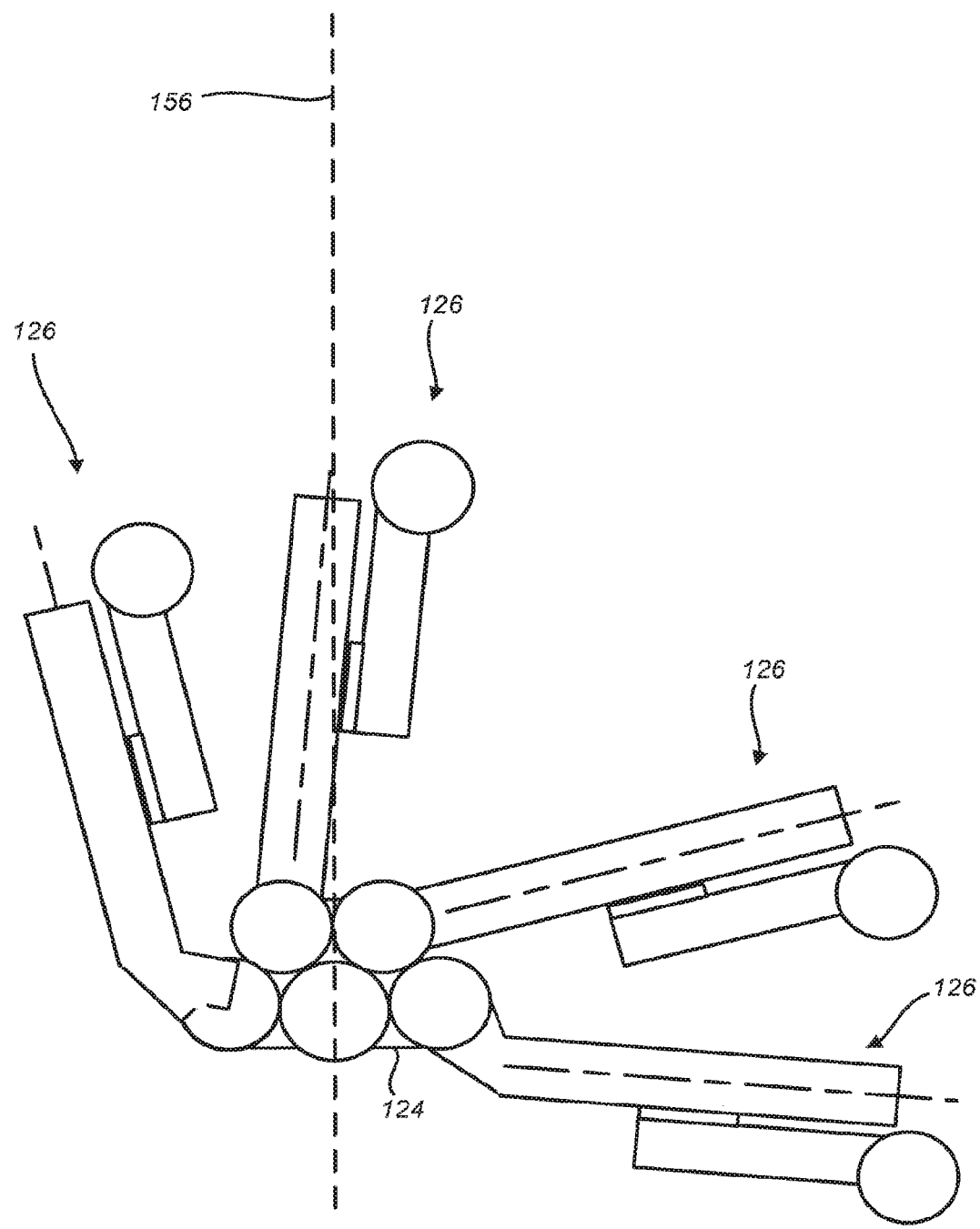
FIG. 9 illustrates rotational orientation limits of set-up linkages relative to an orienting platform of the robotic surgery system of FIG. 8.

FIG. 9 illustrates rotational orientation limits of the set-up linkages 126 relative to the orienting platform 124, in accordance with many embodiments. Each of the set-up linkages 126 is shown in a clockwise limit orientation relative to the orienting platform 124. A corresponding counter-clockwise limit orientation is represented by a mirror image of FIG. 9 relative to a vertically-oriented mirror plane. As illustrated, each of the two inner set-up linkages 126 can be oriented from 5 degrees from a vertical reference 156 in one direction to 75 degrees from the vertical reference 156 in the opposite direction. And as illustrated, each of the two outer set-up linkages can be oriented from 15 degrees to 95 degrees from the vertical reference 156 in a corresponding direction.

Figure 10:
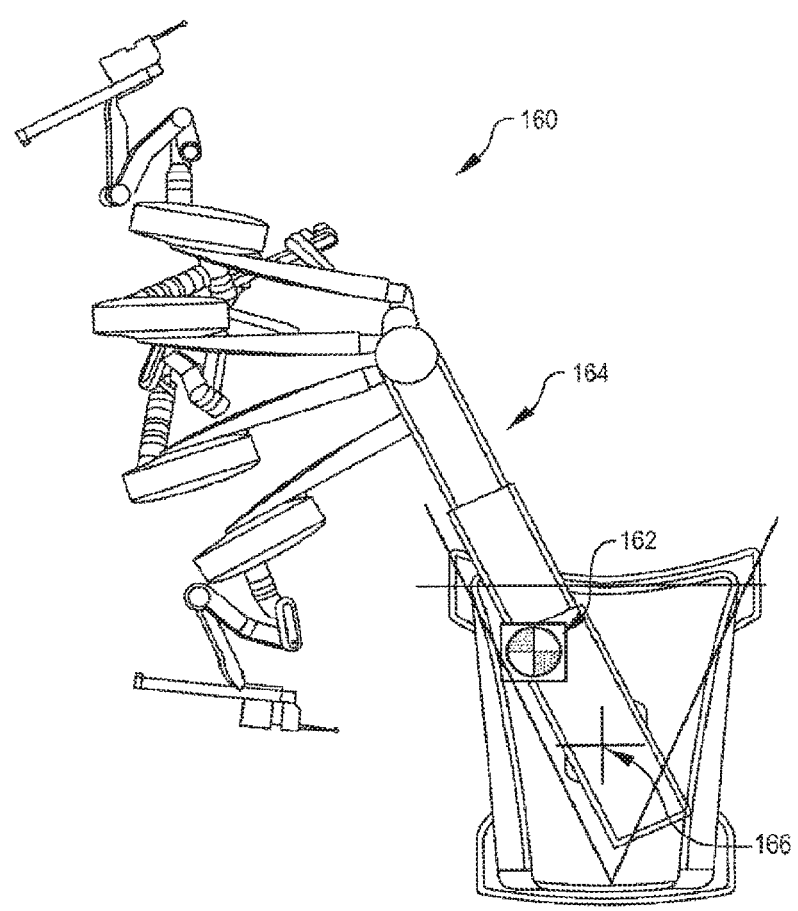
FIG. 10 shows a center of gravity diagram associated with a rotational limit of the boom assembly for a robotic surgery system, in accordance with many embodiments.

FIG. 10 shows a center of gravity diagram associated with a rotational limit of a support linkage for a robotic surgery system 160, in accordance with many embodiments. With components of the robotic surgery system 160 positioned and oriented to shift the center-of-gravity 162 of the robotic surgery system 160 to a maximum extent to one side relative to a support linkage 164 of the surgery system 160, a shoulder joint of the support linkage 164 can be configured to limit rotation of the support structure 164 around a set-up structure (SUS) shoulder-joint axis 166 to prevent exceeding a predetermined stability limit of the mounting base.

Figure 11:
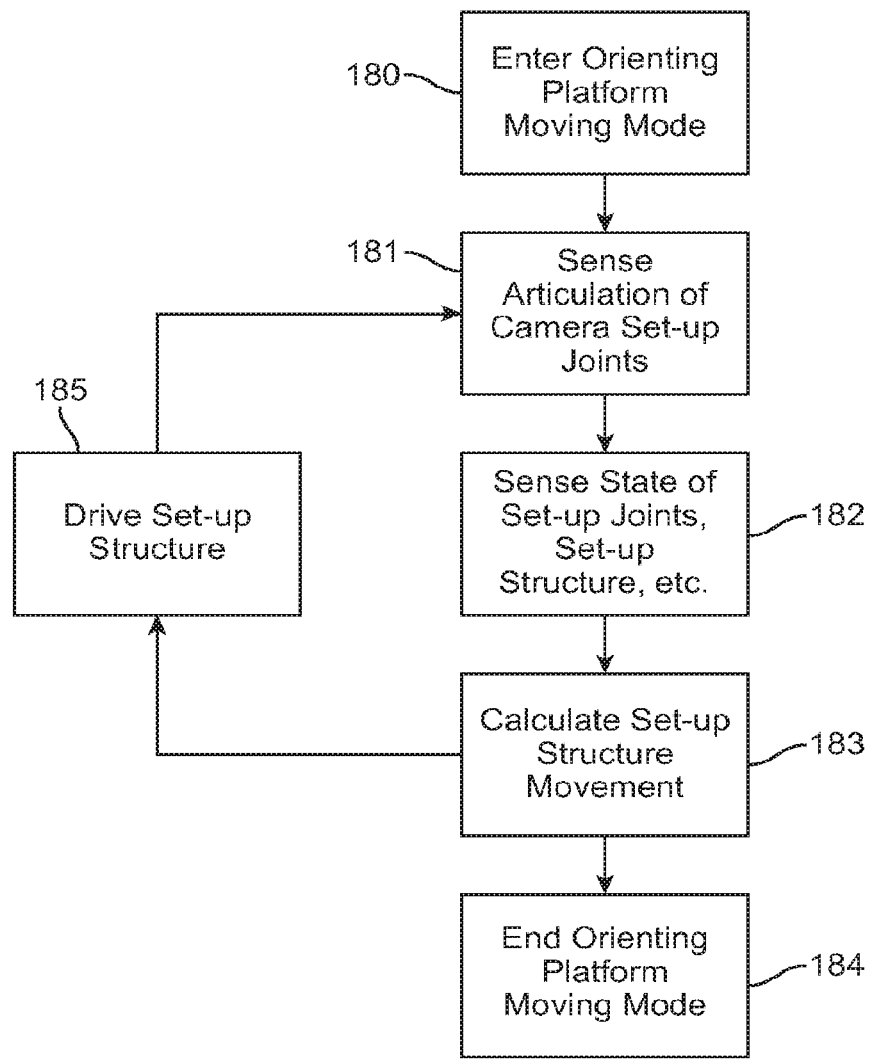
FIG. 11 is a flow chart schematically illustrating a method for preparing a robotic surgical system for surgery by driving an orienting platform in response to movement of a link of one of a plurality of robotic manipulator arms supported by the orienting platform.
Figure 12:
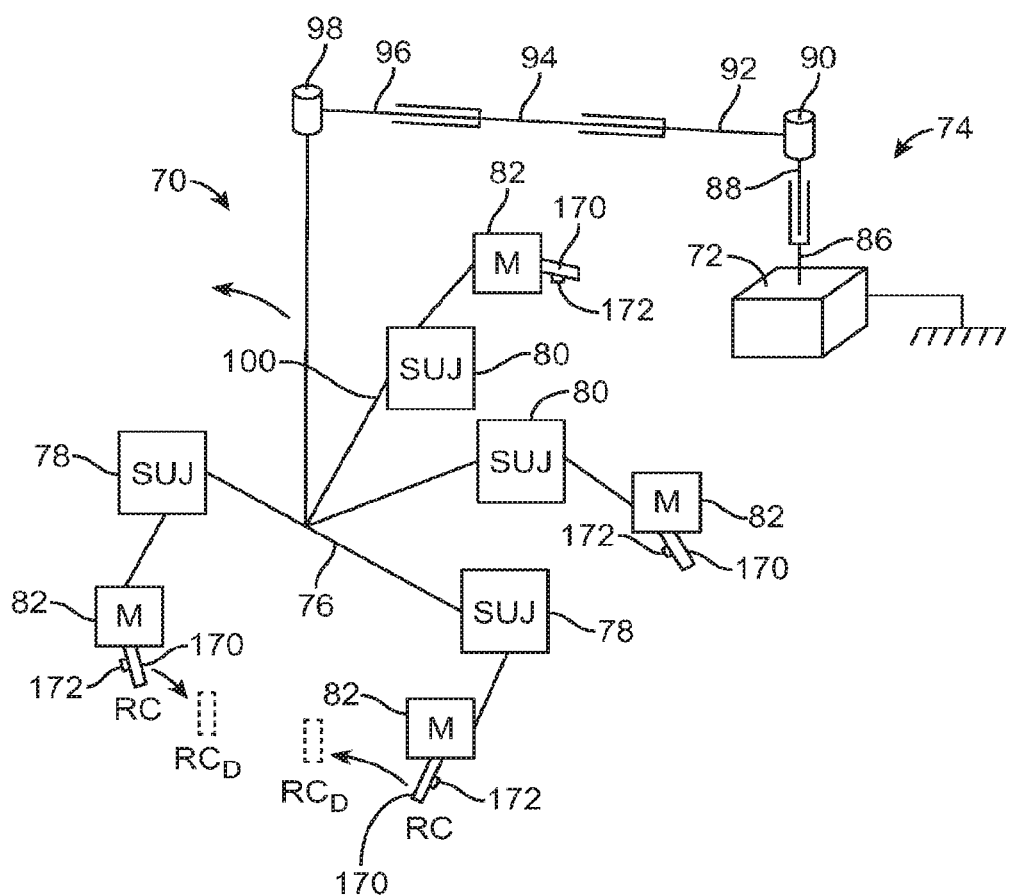
FIG. 12 is a perspective schematic representation of movement of an orienting platform supported by a cart-mounted set-up support structure so as to provide a desired alignment of a plurality of manipulator arms with associated surgical access sites.

Positioning of the Orienting Platform in Response to Manual Articulation of One or More Joints of the Kinematic Chain Supported by the Orienting Platform FIGS. 11 and 12 schematically illustrate a method for driving the orienting platform in response to movement of a link 170 of a manipulator 82 or a link of a set-up joint linkage during set-up of the robotic system for use. In exemplary embodiments, the reference location for movement may not be located on link 170, but may instead be offset relative to link 170. For example, the reference location for movement may be disposed at a remote center location offset from a base (or other structure) of a manipulator linkage, particularly where that manipulator mechanically constrains motion of the manipulator to spherical motion at a fixed remote center location relative to that base. Hence, while the base (or other linkage structure) of the manipulator may serve as an input link 170, the reference location may be spatially separated from the link itself, often at a fixed location in the frame of reference of the link. Optionally, the input link may be a link of a set-up joint linkage 78, 80 configured to support a manipulator 82 relative to the orienting platform 76. For the sake of simplicity, implementations are described below as using movement of link 170 of a manipulator 82 as input. It should be understood however, that in many embodiments, an input link may be a link of a set-up joint linkage 78, 80.

Prior to driving of the orienting platform, the platform will have an initial position and orientation relative to mounting base 72 (depending on the states of the joints of the support linkage 70), and the manipulators will each have an associated location and orientation relative to the orienting platform (depending on the states of the joints of the set-up linkages 78, 80). Similarly, a link 170 of each of the manipulators 82 (and/or a reference location associated with that link) will have a position and orientation relative to the platform 76 which depends on the state of the joints of the manipulator and set-up linkages between the manipulator base (schematically illustrated here by the boxes M) and the platform 76. Link 170 will typically comprise a base of the manipulator, but may alternatively comprise a link kinematically near or adjacent the surgical instrument, such as the instrument holder or carriage. The joint states of the manipulator can generally be described by a pose vector $\theta$.

During set-up, it will often be desirable to move one, some, or all of the links 170 from their initial positions and orientations to desired position(s) and orientation(s) aligned with a surgical site. Additionally, it will often be desirable to start a surgical procedure with the manipulators in a well-conditioned state so as to provide the surgeon with a wide range of motion, help avoid singularities, and the like. In other words, for a given manipulator it will be beneficial to provide both a desired alignment between link 170 and the surgical worksite (including having the remote center RC of the manipulator at or near a desired access site location $RC_D$), and to have the manipulator at or near a desired manipulator state or pose $\theta_D$. Note that the manipulator may already be at or near the desired manipulator pose prior to movement of link 170 or that may be in an initial pose $\theta_I$ significantly different than the desired, well-conditioned pose ($\theta_I \neq \theta_D$). Appropriate positioning and configuring of the manipulators relative to each other may also help avoid manipulator collisions. Where the manipulator is not in a well-conditioned pose prior to alignment with the surgical site, the pose of the manipulator may optionally be altered to a well-conditioned pose before moving the orienting platform, after moving the orienting platform, or while moving the orienting platform. Altering the pose from the initial pose to the well-conditioned pose may be done by manually articulating the joints of the manipulator. Alternatively, there may be advantages to driving the manipulator from the initial pose toward and/or to the well-conditioned pose. For simplicity, the description below assumes the manipulators are in a desired and/or well-conditioned pose prior to initiation of movement of the platform. Regardless, mounting of multiple manipulators 82 to a common platform 76 and driven movement of that platform in response to movement of a link of one of the joints supporting one of the manipulators relative to the platform can facilitate movement of the manipulators into the desired alignment with the surgical space.

The joints of the manipulator will often be maintained in a fixed configuration during movement of the orienting platform and/or manual articulation of the set-up linkages, optionally by driving the motors of each of the joints of the manipulator so as to counteract any manual articulation, by fixing the joint states of the manipulators with joint brakes, by a combination of both, or the like. Hence, while there may be some slight flexing of the links and minor excursions of the joints during movement of the orienting platform and manual articulation of the set-up linkages, the manipulators will typically move as a substantially rigid body. Moreover, the link 170 manipulated by the user and/or to be used as a reference for movement may be any one or more link of (or even kinematically adjacent to) the manipulator or an associated set-up linkage.

Referring now to FIGS. 11 and 12, to enter the orienting platform moving mode 180 of the robotic system processor, an input 172 on or adjacent an associated link 170 may be activated. While Input 172 may optionally comprise a simple dedicated input button or the like, some embodiments may benefit from alternative user interface approaches. As an example, an exemplary input may avoid a dedicated button by instead entering the platform moving mode in response to a set-up joint operation. More specifically, the platform moving mode may be entered by first releasing the set-up joints supporting an associate manipulator so as to allow the remote center (or "port") location of that manipulator to be manually repositioned, a manual movement mode which is sometimes referred to as port clutching. When the manipulator is manually moved to within a threshold of (or in some embodiments actually reaches) a range of motion limit for the released set-up joint linkage, the system may in response enter the platform following mode. Hence, reaching (or approaching) the range of motion limit of the set-up joints becomes a method to request and/or input activation for the entering of the platform movement mode. Input 172 may alternatively be a simple normally off input.

The processor may not enter the orienting platform moving mode despite actuation of the input if a cannula is mounted to the manipulator (or to any other manipulator supported by the orienting platform). While input 172 of a given manipulator 82 is actuated, and/or in response to actuation of input 172, the set-up linkages 78, 80 disposed between that manipulator and the orienting platform will often be unlocked so as to allow manual articulation. This articulation of set-up linkages 78, 80 can be sensed and used as an input for driving the joints of the set-up structure for moving the orienting platform 76. The system will often be balanced about the axes of the set-up linkages so that the user can easily re-orient and/or re-position the manipulator relative to the operating platform, with the manipulator typically moving as a relatively rigid when link 172 is moved relative to the platform and the base 72 of the system. Note that the drive system of the manipulator may be energized and controlled by the processor so as to resist articulation of the joints of the manipulator displacement, or that joint brakes of the manipulator may inhibit articulation, but that some flexing of the manipulator linkages and/or minor excursions of the joints states may still result from the forces imposed on link 172. Note also that in alternative embodiments the joints that are allowed to articulate between link 172 and the orienting platform are powered (such as in a software-center system) those joints may be energized so as to provide movement resistance forces that are sufficiently light so as to allow the link to be manually moved sufficiently for the joint state sensing system of the manipulator to readily identify the desired displacement vector for use as a desired movement input or command from the system user.

Referring still to FIGS. 11 and 12 and as generally noted above, once the orienting platform moving mode has been entered with a particular manipulator 82 to be used as the input device (such as by depressing a switch of input 172), link 170 of that manipulator can be manually moved relative to the platform. Typically, one or more (optionally all) of the set-up joints may be released so as to allow the input movement of link 170 to occur via manual articulation of the released set-up joint(s), optionally while articulation of the linkage of the manipulator is inhibited (such as by driving the manipulator to avoid movement, using a brake system of the manipulator, or the like). Hence, the input may be sensed at least in part as an articulation of one or more joints of the set-up joint system. Still further options may be employed, such as allowing the manual input via a selective combination of articulation of one or more joints of the manipulator and one or more joints of the set-up joint system. Regardless, to facilitate kinematic analysis, provide input for helpful transformations, and the like, the joint states of the set-up structure (including the joints supporting the orienting platform), the set-up joint system, and the manipulator will typically be sensed 182.

Based on the manual input command by the user (as entered by manual movement of link 170 and as sensed via the manual articulation of the joints supporting that link), commands are calculated to move the set-up structure 183. The orienting platform will often be driven per the calculated commands while the user continues to move link 170, so that the base of the manipulators supported by the orienting platform follow the manually moving link. While moving a first manipulator into a desired alignment with the surgical site, the other manipulators may each remain in a fixed pose. Similarly, any set-up linkages between the orienting platform and those other manipulators may also remain locked (and/or otherwise have their articulation inhibited) during movement of the platform. As articulation may be inhibited for all the joints between the links 170 of the other manipulators and the orienting platform, all those other input links (and other structures of the manipulators) follow link 170 of the manipulator for which input 172 is actuated.

The orienting platform may be driven so that the input set-up linkages supporting the input manipulator (for which input 172 is actuated), while the user holds and moves the associated link 170 to a desired alignment with the workspace, are urged to remain in their initial configuration (as per when the system entered the orienting platform mode). The position of the link 170 may continue to be controlled manually by the user during the movement of the orienting platform. In other words, the orienting platform can be moved so that given a current pose θ of the set-up linkages 78, 80 and a current location of the input link 170 (both during movement of the orienting platform), the drive system of the orienting platform moves the orienting platform 185 so that the input set-up linkages 78, 80 are articulated from the current pose toward their initial pose (θ→θi). The effect of this movement of the orienting platform is to largely maintain the initial spatial relationship between the input link 170 and the orienting platform, so that the orienting platform (and all the manipulators supported thereby) follows the input link as it is moved by the hand of the user. The orienting platform movement mode can be terminated 184 by releasing input 172, by mounting a cannula to the input manipulator, or the like. Note that the cannula may not be mounted to the manipulator until after the cannula extends into the patient body, so that it may be desirable for the processor system to inhibit entering of the orienting platform movement mode in response to actuation of input 172 of a manipulator to which the cannula is mounted.

In some implementations of the above method, the orienting platform range of motion may be limited to a subset (e.g., x and y, or z only, etc.) of the full range of motion (e.g., x, y, z, θ). Limiting the range of motion to a subset of the full range of motion may make system set-up more intuitive and quicker for users by reducing the DOFs involved. For example, in some situations, it may be advantageous if the orienting platform movement is limited to vertical positioning movements using the translational column member 82. This may be particularly useful for raising of a teleoperated surgical system over a patient and lowering of the system into a desired position over the patient.

In such embodiments, orienting platform moving mode may be entered 180 for example by manually moving a vertical set-up joint to or near its range of motion (ROM) limit. In some implementations, a ROM limit threshold may be defined so that the platform moving mode is entered when the vertical set-up joint is moved near a ROM limit. Optionally, the moving mode may be entered by moving a vertical set-up joint to or near its ROM limit and/or by a dedicated input button. For example, user may actuate a port clutch input to release the set-up joints to allow free movement of the set-up joints. If the user desires to raise the system, the user may manually move a vertical set-up joint to or near an upper ROM limit to enter the orienting platform moving mode 180. After entering the orienting platform moving mode 180, manual movement of the vertical set-up joint to or near the upper ROM limit may be sensed 181 and set-up structure (e.g., a translational column member 82) movement may be calculated 183 based on sensed states of the set-up joints and set-up structures. The set-up structure (e.g., a translational column member 82) may then be driven (raised) 185 per the calculation. Once there is enough clearance to position the system over the patient, the user may then need to lower the orienting platform of teleoperated system to a height where the manipulators can be positioned in their desired positions. To do so, the user may reverse the sequence of actions (e.g., manually move the vertical set-up joint to or near a lower ROM limit and lead the platform lower in height by lowering the translational column member 82).

While the above implementation is discussed as limiting motion to only the vertical orientation, it should be understood that in some embodiments the motion may be limited to other subsets of the full range of motion. In some embodiments, when a manipulator or a set-up joint is manually moved to or near a ROM limit, the system may first wait a threshold duration of time before entering the orienting platform moving mode 180. The threshold duration of time may avoid inadvertent movement of the orienting platform by manual movement of manipulators or set-up joints by a user. The threshold duration may be for example, 5 seconds or less. In some embodiments, a threshold duration may be 3 seconds. Further, it may be advantageous to provide an audio or visual indicator/alert to a user prior to entering the orienting platform moving mode. For example an audio alert may trigger when a user manually moves the set-up joint to or near a ROM limit. Optionally, the audio or visual alert may be configured indicate a duration of time that the set-up joint has resided at or near the ROM limit to provide the user information on when the system will enter the orienting platform moving mode. For example, an audio indicator may provide a countdown or discrete beeps for each second. If the manipulator or the set-up joint is manually moved to or near a ROM limit and released at or near the ROM limit before entering the orienting platform moving mode 180 or after exiting the orienting platform moving mode 180, it may be advantageous to provide control software and/or hardware for pushing the manipulator and/or set-up joint away from the ROM limit as will be discussed in more detail below.

In some embodiments, one or more joints of the set-up structure may be programmed with upper limits to their respective range of motion. The upper limits may be programmed into one or more of the set-up structure joints due to room constraints. For example, in some situations, it may be beneficial to program a translational column member 82 with an upper limit when room ceiling heights limit the full range of motion of a translational column member 82. Optionally, when a set-up structure joint is so limited, the motion of the orienting platform during the orienting platform moving mode may similarly be limited. For example, when raising an orienting platform by manually moving a vertical set-up joint to the upper ROM limit, the system may limit the orienting platform from being raised further if the translational column member 82 reaches a preprogrammed upper limit. While some embodiments may prevent set-up structure motion beyond a programmed limit during orienting platform movement in the orienting platform moving mode, other embodiments may be provided where the movement of the orienting platform due to manual movement of a manipulator or set-up joint by a user may override a programmed limit to range of motion of a set-up structure.

Orienting platform 76 may support manipulators 80, 82 in beneficial relative positions for many procedures. Hence, once a link 170 of a first manipulator 80 has been moved to a desired alignment with a surgical worksite, the instrument holders and the like of the other manipulators will often be at or near associated desired initial alignment for their associated surgical tools, and only limited additional repositioning of the manipulators may be warranted. Minor adjustments to a particular manipulator alignment may be accommodated by releasing a brake system of the set-up joint arm supporting that manipulator relative to the orienting platform and moving that manipulator as desired relative to all the other manipulators. For example, once a camera manipulator is used to position the orienting platform and to initially align all the instrument manipulators, the set-up linkages between each instrument manipulator and the orienting platform can be released and the released manipulator position can be adjusted independently if needed. In an exemplary embodiment of orienting platform movement mode, sensing of the manual movement of a first input link 170 effectively senses movement of the manipulator from an initial remote center RC to a desired remote center $RC_D$. Movement of the orienting platform moves the remote centers RC of the other manipulators toward their associated desired remote centers $RC_D$. Additional adjustment of those other remote center locations can then be performed by sequentially releasing each of the set-up linkages of the associated manipulator and moving the released manipulator so as to provide the desired alignment between the released manipulator RC and the desired remote center $RC_D$.

Calculation of the Orienting Platform Movement Commands

Figure 12A:
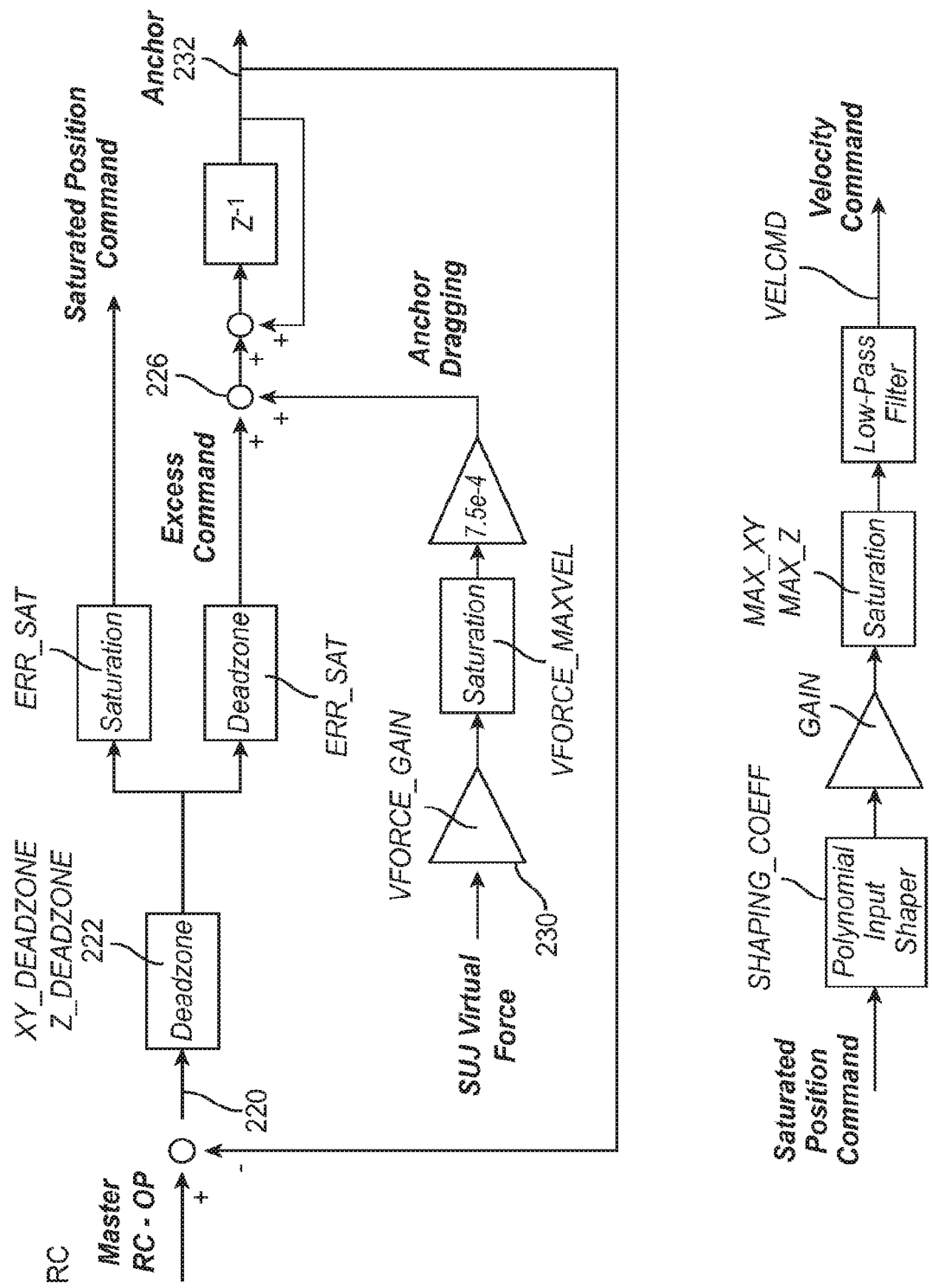
FIGS. 12A and 12B are block diagrams illustrating controllers used as components of the orienting platform drive system, and particularly showing an exemplary software system arrangement of the processor.
Figure 12B:
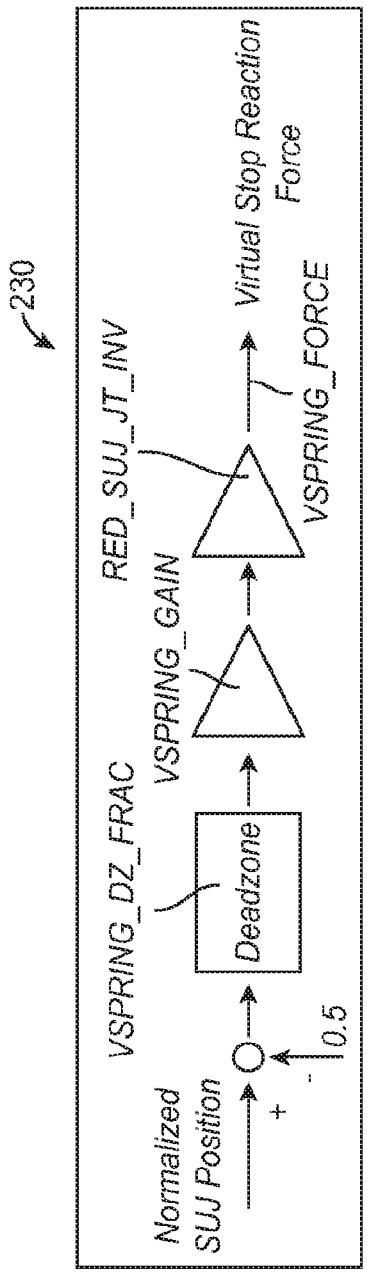

Referring now to FIGS. 12A and 12B, an exemplary software structure and/or processor arrangement for calculating the movement commands of the orienting platform can be understood. As the orienting platform and other manipulators will often follow the movement of the input link 170 for which the orienting movement input 172 has been actuated, the overall movement is somewhat analogous to (and is sometimes referred to herein as) a "Lead-the-Horse-By-the-Nose" (LHBN) control mode. The LHBN control mode allows the user to move the operating platform 76 and drive the setup-structure by manually moving the remote center of a floating manipulator 82. In a basic form, the control objective is to move the operating platform 76 such that the manipulator 82 remote-center remains at a desired location in the operating platform 76 frame. Thus, when the user manually displaces the manipulator 82 in the world frame, the controller can move the operating platform 76 and its frame through the same displacement to drive the error between the actual remote center and the desired remote center to zero.

The raw error between the actual remote center RC and desired remote center $RC_D$ locations form the input command 220 to the LHBN controller, as shown in FIG. 12A. A small dead zone 222 (less than 10 cm, often about 3 cm or less) is applied to the error signal before scaling the error into a raw velocity command. A low-pass filter (of between about 0.1 Hz and 10 Hz, typically approximately 1 Hz) generates a band-limited velocity command. The command is then saturated 224 to create the velocity command in the operating platform frame. When LHBN mode is entered a half cosine shaped scaling is applied to the command over a short window to ramp up the command in a smooth manner. Similarly, the command is scaled by a half cosine shaped scaling in the reverse direction when the mode is exited to smooth the deceleration. The velocity command, after startup/shutdown scaling, is provided to the setup structure's inverse kinematics. Further trimming of the velocity command may occur in the inverse kinematics calculations when joints are at or near their limits.

The desired remote center location $RC_D$, also referred to herein as the anchor, is established when LHBN control mode is entered. When the LHBN control mode is initiated, the desired remote center $RC_D$ and actual remote center RC are co-located, thus starting the mode with zero error (so that the platform will not move unless and until the input link 170 moves relative to the orienting platform). Manual movement of the link 170 while in the LHBN control mode causes the platform to be driven so that the actual remote center RC generally remains at the desired remote center $RC_D$ in the frame of the operating platform. Several enhancements to the basic LHBN operation may optionally slide or alter the location of the anchor or desired remote center $RC_D$ relative to the actual remote center to tweak the behavior. The anchor can, for example, be moved by commanding an anchor dragging velocity and integrating as indicated in FIG. 12A. One anchor velocity input may be the difference between the saturated and unsaturated velocity command 226. The purpose of this feature may be to avoid large saturated velocity commands. Once the velocity command reaches saturation, any additional input motion of the remote center drags the anchor (or moves the $RC_D$ relative to the orienting platform) to keep the command just at the saturation limit. Intuitively, the error between the anchor and the remote center can be visualized as a ball, and dragging the anchor means dragging the ball's center around whenever the error vector reaches the ball's radius.

Motion away from range of motion limitations or hard stops of set-up linkages 78, 80 is also achieved through anchor dragging, as can be understood with reference to the block diagram model shown in FIG. 12B. Some automatic motion of the set-up structure 74 away from hardstops is desirable as the user may not otherwise be able to easily manually command the desired set-up structure motion. In one embodiment, a subroutine may compute a virtual force 230 acting on the platform 76 that mimics springs installed at the limits of motion of the set-up linkages 78, 80. The force can be referred to as a port-dragging force. A virtual force may be transmitted from each configured manipulator 82 to enable the setup structure controller to back away from setup joint range of motion limits. The LHBN control mode software can scale the port-dragging virtual force from the input manipulator 82 and add this quantity to the anchor dragging velocity. The effect is to create a command 232 to drive the set-up structure 76 to move away from hardstops of set-up linkages 78, 80.

Some or all of the gains, saturations, and/or deadzones used in the LHBN control mode are optionally tunable. For example, in some embodiments, the platform range of motion may be limited to a subset of the full range of motion when the platform is moved in a platform movement mode. As described above, such methods and systems may make system set-up more intuitive and quicker for users by reducing the DOFs involved. In such an embodiment, the gains for some of the directions may be tuned to zero. For example, in embodiments where only platform vertical movement is controlled during a platform movement mode, the gains for an x-direction movement and a y-direction movement may be set to zero so that only z-direction movement data is provided. Each parameter in FIGS. 12A and 12B is listed in the following Table:

XY_DEADZONE, Deadzone applied to input motion in the x-y plane
Z_DEADZONE, Deadzone applied to input motion in the z direction
ERR_SAT, Maximum error input. Error beyond this value is saturated
VFORCE_GAIN, Scaling of virtual forces from setup joints into anchor dragging velocity
VFORCE_MAXVEL, Saturation of anchor dragging velocity
SHAPING_COEFF, Coefficients of the polynomial that shapes the saturated position command
GAIN, Gain from position command (error signal post deadzone and saturation) and the LHBN velocity command
MAX_XY, Maximum velocity command in the xy plane
MAX_Z, Maximum velocity command in the z direction
VELCMD, Final velocity command
VSPRING_DZ_FRAC, Deadzone fraction of each setup joint range of motion
VSPRING_GAIN, Gain from position to virtual joint force outside the deadzone of each joint
RED_SUJ_JT_INV, Inverse transpose of the setup joint Jacobian.
VSPRINT_FORCE, Final virtual force reflected to the OP The virtual spring force used to move the set-up structure linkage away from set-up joint linkage hard stops can be calculated as shown in FIG. 12B, and the deadzone fraction may determine how much of the range of motion produces no virtual force. Note that the deadzone fraction should be less than unity and that the active portion may be split evenly between the two hardstops on each joint. If the user moves the remote center such that a setup joint is against a hard-stop, anchor dragging can be used to integrate the virtual force and increase the velocity command to move away from the hard-stop. A smoothly increasing velocity command will be generated that moves the setup structure away from the from the setup joint range of motion limit. The velocity command will increase until saturation is reached at which point a steady-state velocity of the setup structure will be maintained.

Thus a large gain on the virtual force will drive the error significantly into saturation. For more description of the kernel keys involved in the calculation of the virtual force, see the Table above.

Figure 12C:
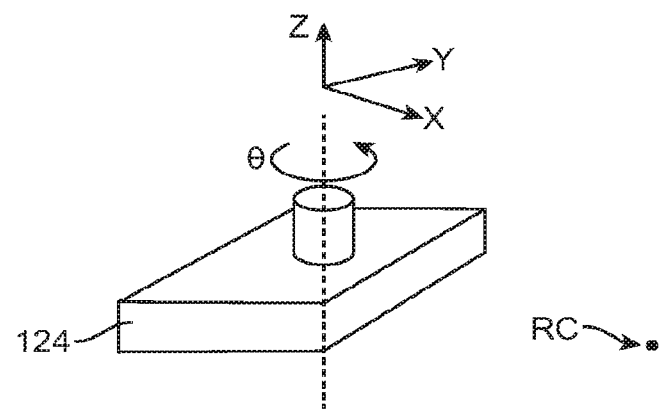
FIGS. 12C and 12D are a schematic representation of an orienting platform showing an associated coordinate system and degrees of freedom; and a perspective representation of an orienting platform supported by a ceiling gantry set-up support structure so as to provide a desired alignment of a single manipulator arm with an associated surgical access site.

Referring now to FIG. 12C, an alternative drive system for the set-up structure and orienting platform 124 preferably allows movement along x, y, and z axes to drive a manipulator RC to a desired position relative to the orienting platform. By manually moving one or more link of a manipulator 82 in space (and optionally by moving the entire manipulator), the user can cause the operating platform to follow by just computing the error vector between the desired manipulator RC position (in the orienting platform frame of reference) to the actual manipulator RC position and using this vector to generate desired x, y, z velocities.

Figure 12D:
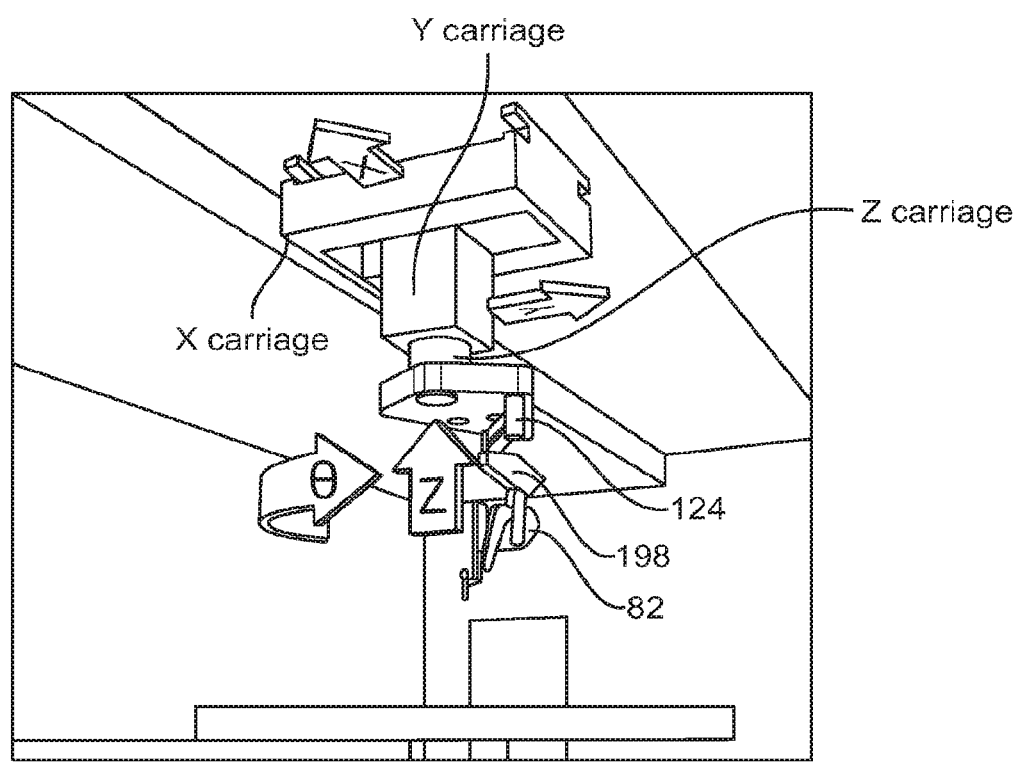

Referring now to FIGS. 12C and 12D, methods for moving the x, y, z, and θ axes of the orienting platform will generally seek to achieve a desired positioning of the orienting platform 124 and one or more manipulators 82 mounted thereon so as to provide a well-conditioned manipulator pose when starting a surgical procedure (with the various degrees of the freedom of the manipulator being desirably near their centers of range of motions while the tool is in a desired location of the surgical workspace, with the manipulator kinematics being well away from motion-inhibiting singularities, and the like). Along with orienting platforms supported by cart-mounted set-up structures such as those described above, ceiling mounted set-up structures 190 and other driven robotic linkages with one, two, three, four, or more degrees of freedom may be employed. Similarly, the input for motion may optionally be input by manually articulating a passive joint (such as one of the joints along the set-up joint structure described above) and/or one or more actively driven joints (such as a joint of the manipulator 80, 82). Hence, while the systems may be described with reference to a few exemplary robotic kinematic structures, the control techniques may apply well to a range of other robotic systems having redundant degrees of freedom and/or large numbers of joints, and are particularly interesting when considering such systems that have a mix of active and passive joints; systems with one set of joints that are driven during set-up and another different set (with or without some overlapping members) of joints that are driven during surgery; systems in which individual manipulator controllers exchange only limited state information; and the like.

To use the robotic capabilities of the system during set-up, the processor of the robotic system may include software implementing a mode in which the robotic structure is driven toward and/or maintains a desired relationship or pose between the orienting platform and the manipulator remote center during manual movement of a link of the manipulator. This algorithm, when active, takes as its inputs the actual and desired relationships between the orienting platform and the manipulator remote center and drives the actual pose to the desired one, optionally without disturbing the position and orientation of the manipulator remote center. In other words, as the user moves the passive axes around, the active axes may optionally follow in such a way so as to achieve or maintain a specific robot pose.

Figure 13:
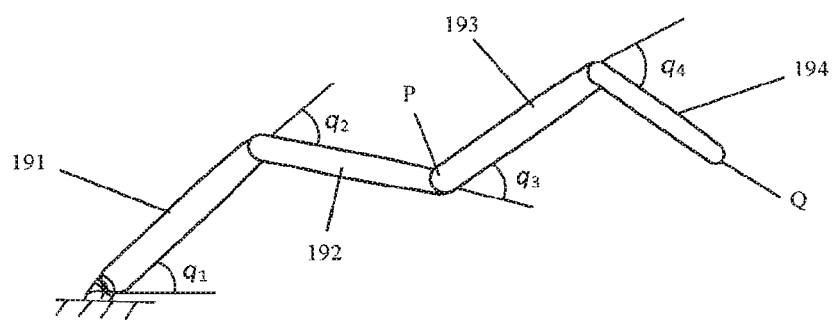
FIG. 13 schematically shows a simplified four joint planar passive/active robotic kinematic system in which active joints are driven in response to deflection of passive joints.

The simplified 4-link manipulator shown in FIG. 13 helps to explain one embodiment of the control structures and methods described herein. In this schematic manipulator, links 191 and 192 are active, meaning that $q_1$ and $q_2$ are controlled by a controller, while links 193 and 194 are passive, and can be moved by hand. Point Q is a point on the robot of direct interest to the user, and is positioned manually to a user-specified target location relative to the robot base. Hence, point Q may correspond to the remote center of the manipulator, and the user would typically position point Q so that the manipulator could, for example, be connected to the camera cannula, which may already be installed in the patient or which may be inserted in the patient after the robotic structure is moved into position. For various reasons (including maximizing usable range of motion, minimizing collisions, etc.) it is often desirable to obtain a specific relationship between P and Q. As long as joints $q_3$ and $q_4$ are free, and there is sufficient range of motion and the manipulator is not near a singularity, P can translate independently of Q, so the controller is free to establish the desired relationship if Q is simply held fixed relative to the base. This principle can be taken advantage of to automatically establish the P to Q relationship while the user holds Q fixed in space. It is also possible to continuously run this automatic positioning algorithm, so that as a user manually adjusts the position of Q, the active axes $q_1$ and $q_2$ move in such a way so as to maintain the desired P-Q relationship.

In the simplified example of FIG. 13, two active and two passive degrees of freedom are shown, and the only quantities of interest were the relative positions in the plane of P and Q. Ceiling and/or cart mounted robotic surgical systems will often be more complex: there are seven active degrees of freedom (four on the gantry and three relevant axes on the ECM) in the embodiment of FIG. 12D, and three passive axes (schematically shown by the set-up joints 198 between the orienting platform 124 and the manipulator 82), for a total of ten degrees of freedom. Maintaining the manipulator remote center end point location and orientation is often a six DOF issue, which leaves us with four extra degrees of freedom (DOFs) with which to perform our internal optimizations in this embodiment. Note that for purposes of this discussion, the exact nature of what is considered desired may include any number of criteria, and many concept described here can be applied regardless of the method used to determine the optimal target location. One strategy for performing this sort of optimization is to consider the entire system as a single 10 DOF redundant manipulator. One can then use a technique of imposing a primary, inviolable goal paired with a desired auxiliary goal of minimizing a cost function. The primary goal in our case may be to maintain the position and orientation of the manipulator remote center relative to the room and the auxiliary goal may be to achieve the optimal relationship between the orienting platform and the manipulator.

A second strategy is to segment the problem into two parts:

1) A set-up structure optimization problem that seeks to minimize a cost function. This cost function is configured to achieve a minimum when the orienting platform position and orientation reaches an optimal or desired location relative to the manipulator RC.

2) A manipulator regulation problem that seeks to maintain a constant manipulator orientation relative to the room. This second strategy benefits from the fact that the only information that needs to be shared between the ECM and Gantry manipulator is the location of the base and tip of each—it is not required to know the position of every joint. This lends this particular strategy a nice advantage in that it requires less communication bandwidth between manipulators.

Figure 14:
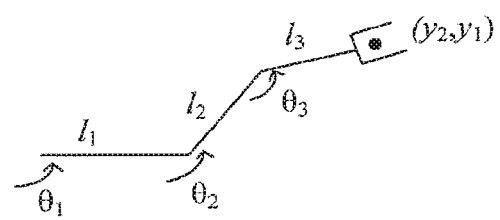
FIG. 14 schematically shows a simplified three link planar joint system for use in describing kinematic analysis of the desired joint control.
Figure 15:
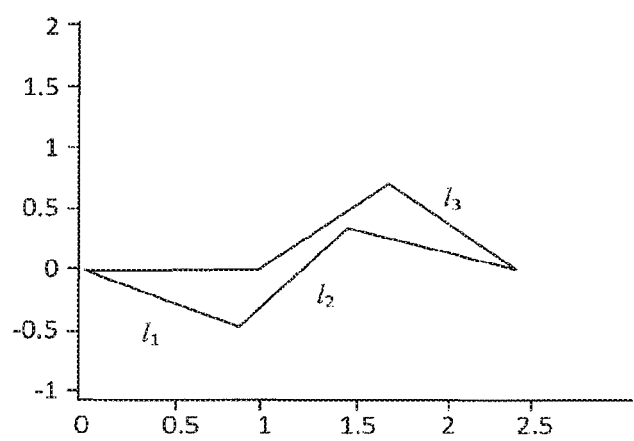
FIG. 15 graphically shows movement of a simplified planar kinematic system through its null space so as to demonstrate driven motion of a set-up structure supporting a manually articulatable joint system in response to manual articulation of one or more of those joints.

We now provide the mathematical framework necessary to move the setup structure without moving the remote center. Referring now to FIGS. 14 and 15, reconfiguring a simplified planar set-up structure linkage to a desired pose may be modeled as moving the manipulator through its null space (per the description above of FIG. 13, so that Q remains invariant while P is driven to a desired x and y location in space). Mathematically, where the lengths of links 1-3 FIG. 14 are $l_{1-3}$, the Jacobian matrix and joint position vector q can be identified as:

$$x = l_1 c_1 + l_2 c_{12} + l_3 c_{123}$$

$$y = l_1 c_1 + l_2 s_{12} + l_3 s_{123}$$

$$J = \begin{bmatrix} -s_1 - s_{12} - s_{123} & -s_{12} - s_{123} & -s_{123} \\ c_1 + c_{12} + c_{123} & c_{12} + c_{123} & c_{123} \end{bmatrix}$$

$$q = \begin{bmatrix} \theta_1 \\ \theta_2 \\ \theta_3 \end{bmatrix},$$

The following is a decomposition of the joint velocities as a sum of end-effector motion and internal joint motions that result in no end-effector motion.

$$\overset{\circ}{q} = \underbrace{J^t \vec{v}}_{\substack{\text{Desired} \\ \text{Cartesian} \\ \text{motion}}} + \underbrace{(I - J^t J)\overset{\circ}{\vec{q}}_0}_{\substack{\text{Desired internal} \\ \text{motion through Null} \\ \text{Space of manipulator}}}$$

Set $\vec{v} = [\vec{o}] \rightarrow$ meaning, we do not want end effector to move Set $\overset{\circ}{\vec{q}}_0 = \begin{bmatrix} \overset{\pi}{q}_{\theta_1} \\ 0 \\ 0 \end{bmatrix} \rightarrow$ meaning move $\theta_1$ at velocity $\overset{\pi}{q}_{\theta_1}$. Don't care what $\theta_2$ and $\theta_3$ do, as long as these internal motions do not move end effector Hence, we can move $\theta_1$ and did not have to specify $\theta_2$ and $\theta_3$ to move the manipulator through the null space without changing end effector position. Similarly from a Matlab simulation, we see that we can move an axis through the Null space without having to specify the other joints. While the proceeding demonstrates optimization of planar set-up joints, the framework extends to orientation.

As discussed above, the orienting platform moving mode may be entered 180 by manually moving a set-up joint to or near its range of motion (ROM) limit. If the platform moving mode is entered with the set-up joint at its range of motion limit (such that the set-up joint is restricted in further movement in at least one of its degrees of freedom), it may be desirable to provide a virtual force that acts on the platform 76 (also referred to as a port-dragging force) to move the platform 76 relative to the set-up linkages to back the set-up joint away from the range of motion limit. This allows the set-up linkage additional leeway move toward its range of motion and the system may use the further movement of the set-up joint toward its range of motion limit as an input for moving the orienting platform using the methods described above.

While it may be advantageous to provide the virtual force that acts on the platform after entering the orienting platform moving mode, it may also be preferable to provide virtual springs and/or physical springs at the range of motion limits of a joint that act on the joint during manual movement of the joint (e.g., before, during, or after orienting platform movement mode). As mentioned above, it may be desirable to keep one, some, or all joints of the kinematic chain off a "hardstop" or physical range of motion limit (ROM limit) associated with the joint or otherwise maintain a desired range of motion for one, some, or all joints of the kinematic chain when exiting the set-up mode. For example, it may be beneficial to keep joints of the kinematic chain off a ROM limit as a safety feature of a surgical system. In a system with redundant degrees of freedom (DOFs), if a relatively more distal joint is at a ROM limit (e.g., fully compressed), and then one or more relatively more proximal joints are moved in a DOF redundant to the distal joint, the arm distal of the distal joint may exert extremely high forces against an object (e.g., operating table or the like) or patient. Accordingly, it may be beneficial to push the joint from a physical ROM limit or to otherwise maintain a desired range of motion of the joint so as to provide a buffering zone between the joint and the physical ROM limit. In some embodiments, control systems may detect movement of the joint within the buffering zone, in which case the system releases a driving or a braking by an associated drive or brake system so as to allow one or more physical and/or virtual springs to absorb and counter excess motion. This may beneficially reduce the amount of force exerted by manipulators, links, and/or instruments distal from the joint.

Accordingly, in further embodiments, hardware or software may be used to move set-up joint linkages from their range of motion limits even outside of the platform movement mode (or LHBN). The hardware may be physical springs installed at the range of motion limits, bumpers installed at the range of motion limits, and/or a tunable spring acting on the set up linkage and combinations thereof. Additionally, it should be understood that in some embodiments, it may be preferable to use a combination of virtual springs (software subroutines for generate virtual forces), tunable springs, bumpers, and/or other physical springs for pushing a set-up joint linkage from its range of motion limit. Moreover, control methods may be implemented for actuating and/or delaying an actuation of a drive or brake system associated with the set-up linkages to facilitate pushing set-up joint linkages from their range of motion limits and maintaining a desired spacing from the range of motion limits.

Figures 16, 17, 18:
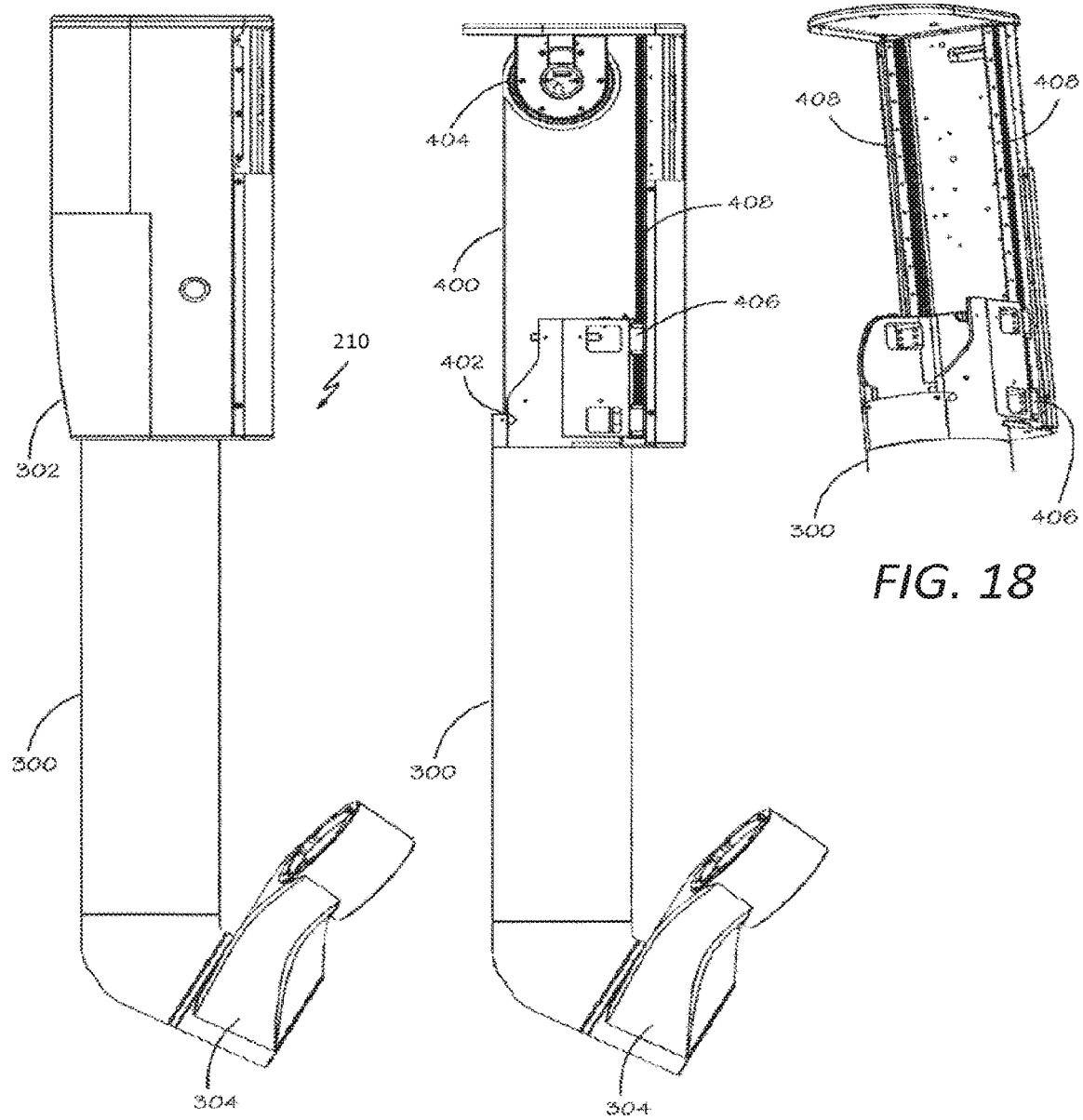
FIG. 16 is a side view of setup joint for a surgical instrument.
FIG. 17 is a side view of the setup joint shown in FIG. 16 with a housing removed.
FIG. 18 is a perspective view of a portion of the setup joint shown in FIG. 17.

FIG. 16 illustrates a side view of an exemplary set-up joint 210 that may include physical springs, tunable springs and/or bumpers for pushing joint 210 away from its range of motion limits. A vertical column 300 hangs down from a housing. An arm 304 is supported by the lower end of the vertical column 300. The arm 304 in turn supports the surgical manipulator and its associated teleoperated actuators. A surgical instrument may be coupled to the surgical manipulator and be supported in turn by the arm 304 and the vertical column 300.

FIG. 17 is a side view of the extensible support 210 shown in FIG. 16 with the cover 302 removed from the housing. The upper end of the vertical column 300 is coupled to a sliding assembly, such as a track 408 and carriage 406 assembly that allows the vertical column 300 to move up and down to adjust the height of the surgical manipulator over the patient.

FIG. 18 is a perspective view of the housing portion of the extensible support shown in FIG. 16. Some components have been removed to allow the track 408 and carriage 406 assembly to be seen more clearly.

Referring again to FIG. 17, a constant force spring 400 is coupled to the vertical column 300 at a lower end 402 of the constant force spring 400. The constant force spring 400 is rolled around a drum 404 that is supported by the upper end of the extensible support assembly 210. The constant force spring 400 counteracts the force of gravity acting on the vertical column 300 and the structures it supports including the surgical instrument.

Constant force springs may be constructed as a rolled ribbon of spring steel such that the spring is relaxed at a lower stress state when rolled up as opposed to being extended. As it is unrolled, the restoring force comes primarily from the portion of the ribbon near the roll of relaxed spring. Specifically, the force comes from the region that is being transitioned from round to flat. No force comes from the portion that is totally unrolled, or still rolled on the drum 404. Because the geometry of that region remains nearly constant as the spring unrolls, the resulting force is nearly constant. A self-retracting steel measuring tape is an example of a constant force spring. While the constant force spring 400 provides a nearly constant counter-balancing force to support vertical column 300 and the attached structures, it would desirable to provide a counter-balancing force that is more constant than what can be achieved with a constant force spring alone and which can compensate for differing supported weights.

Figure 19:
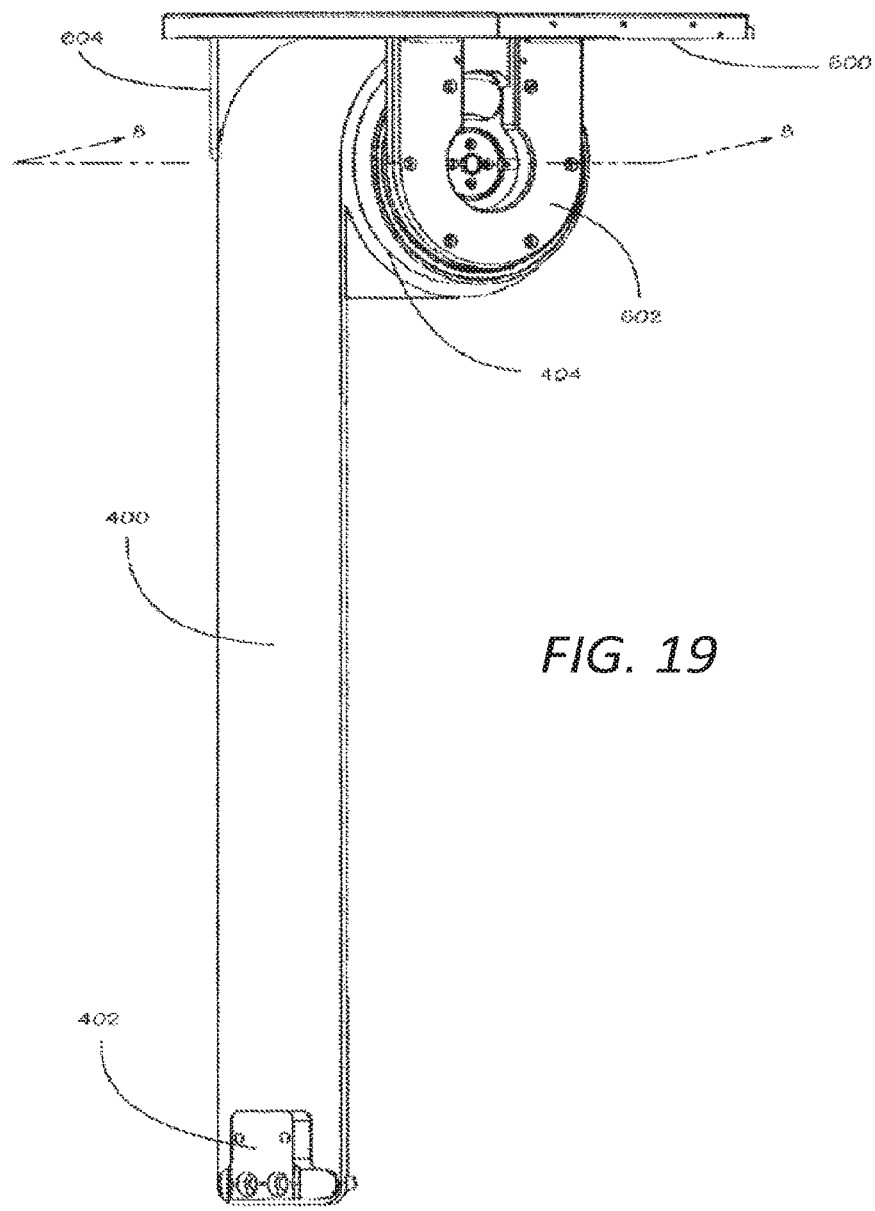
FIG. 19 is a perspective view of a constant force spring assembly.

FIG. 19 is a perspective view of the constant force spring 400 shown in FIG. 17. A bracket 600, 602, 604 is supported by the upper end of the extensible support assembly 210. The bracket rotatably supports the drum 404 around which the constant force spring 400 is rolled. The constant force spring 400 may be fixed to the drum 404 by the friction force created between the surface of the drum 404 and the constant force spring 400 as it attempts to fully roll up to a relaxed diameter that is smaller than the drum diameter.

Figure 20:
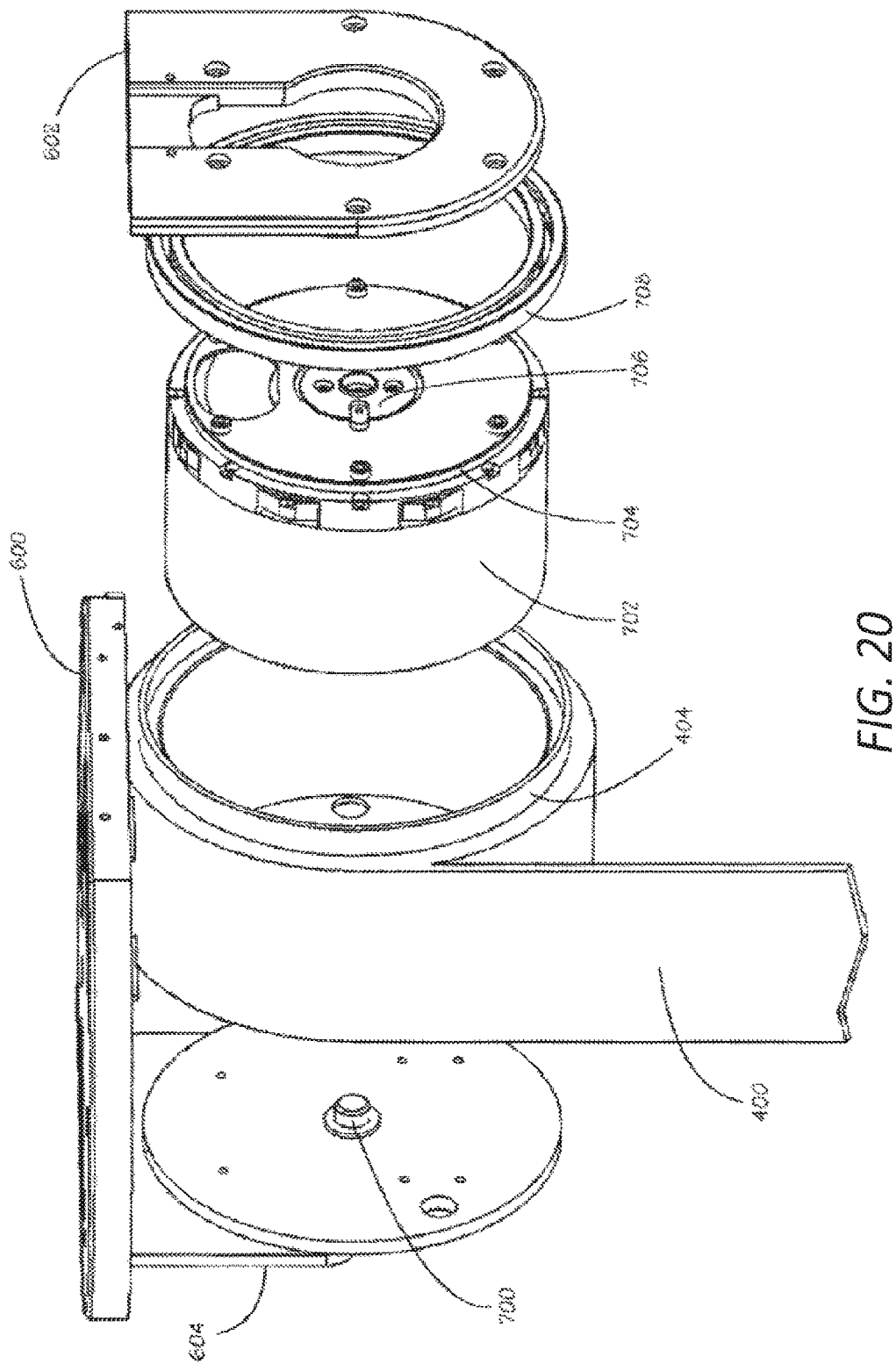
FIG. 20 is an exploded perspective view of a portion of the constant force spring assembly shown in FIG. 18.

FIG. 20 is an exploded view of the drum portion of the constant force spring assembly shown in FIG. 18. A plate that includes an axial support 700 is fixed to one side 604 of the bracket that supports the drum 404 from the upper end of the extensible support assembly 210. The axial support 700 may provide a bearing that rotatably supports the drum 404. The constant force spring assembly includes a motor, which may be a brushless DC motor, having a stator 702 and a rotor 706 that provides an active rotational force that turns the drum 404. The force provided by the motor is translated into a linear force acting on the vertical column 300. The torque provided by the motor is translated into a linear force across the constant force spring 400 acting on the vertical column 300. The torque provided by the motor may add to or subtract from the counterbalancing force provided by the constant force spring 400.

The motor includes a stator 702 that is fixed to a second side 602 of the bracket that supports the drum 404. A bearing 708 may be supported by a portion 704 of the motor stator to provide a rotatable support for the drum 404. The motor further includes a rotor 706 that is fixed to the drum 404.

Figure 21:
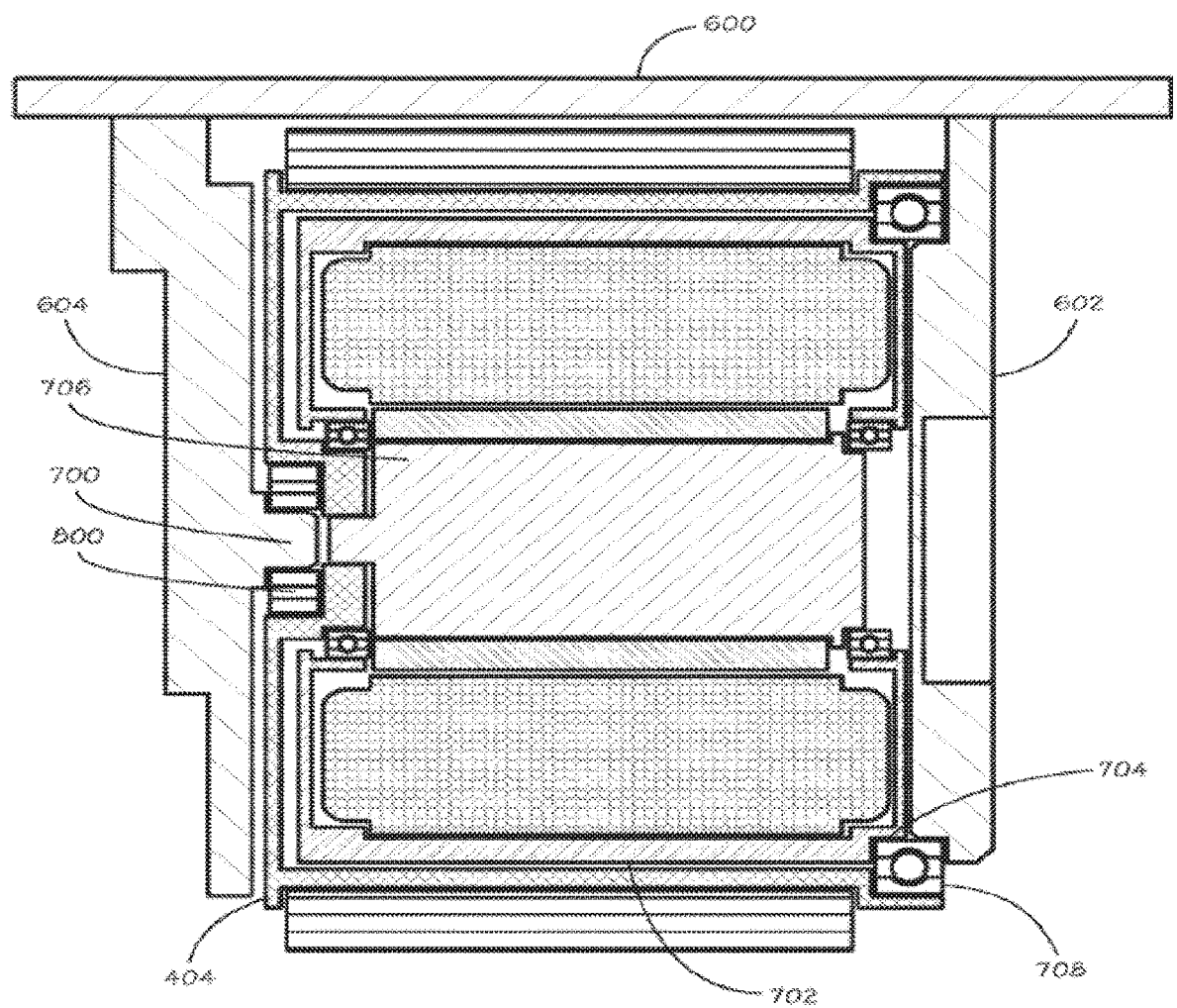
FIG. 21 is a cross-section view of a portion of the constant force spring assembly taken along line 8-8 in FIG. 18.

FIG. 21 is cross-section view of the drum portion of the constant force spring assembly taken along section line 8-8 shown in FIG. 19. As can be seen in this view, The bracket 600,602, 604 and the motor stator 702 which are fixed together as one sub-assembly. The bracket and motor provide a ground reference for the rotating drum 404 and motor rotor 706 which are fixed together as a second sub-assembly.

A first bearing 800 that is supported by the axial support 700 on the bracket 604 supports a closed end of the drum 404. Providing a closed end to the drum 404 may increase the strength of the drum 404 so that it can support the rolling force of the constant force spring 400 when rolled onto the drum 404 prior to being assembled with the motor. A second bearing 708 that is supported by a shoulder 704 on the motor stator 702 supports an open end of the drum 404. Thus the drum 404 and motor rotor 706 are supported by bearings 708, 800 that are in turn supported by the grounded bracket 600,602, 604 and motor stator 702. In other embodiments, other arrangements may be used to rotatably support the drum 404 and motor rotor with respect to the bracket and motor stator 702.

In other embodiments, the motor may be provided in locations other than the interior volume of the drum that supports the constant force spring. For example, the rotor of the motor may be extended by a shaft that is directly coupled to the coaxial drum. Alternatively, the drum and the motor may not be coaxial and the rotor of the motor may be coupled to the drum by a mechanical transmission such as a belt, gears, and/or a chain and sprocket drive. It is also possible to fix what has been identified as the motor rotor to the bracket and couple the drum to what has been identified as the motor stator. In this configuration the outer part of the motor and the coupled drum rotate around the inner part of the motor.

It will be appreciated that the constant force spring 400 could be replaced by a flat belt and the motor could provide the force to counterbalance the force of gravity acting on the vertical column 300 and the structures it supports including the surgical instrument. However, this would require a sizeable motor and a substantial amount of electric current to support mechanisms that may weigh perhaps twelve to twenty-four kilograms. By providing a constant force spring as the coupling between the motorized drum and the load, the constant force spring provides the majority of the force required to support the load. The motor provides a biasing force that corrects for the variability of the load and the irregularities in the force provided by the constant force spring.

In one embodiment, the constant force spring 400 is sized to provide slightly more than the force required to support the heaviest load. Thus the constant force spring 400 will always lift the load. The motor is used to provide a controllable downward force that acts against the force provided by the constant force spring 400 to provide a "neutral buoyancy" for the vertical column 300 and the structures it supports.

Figure 22:
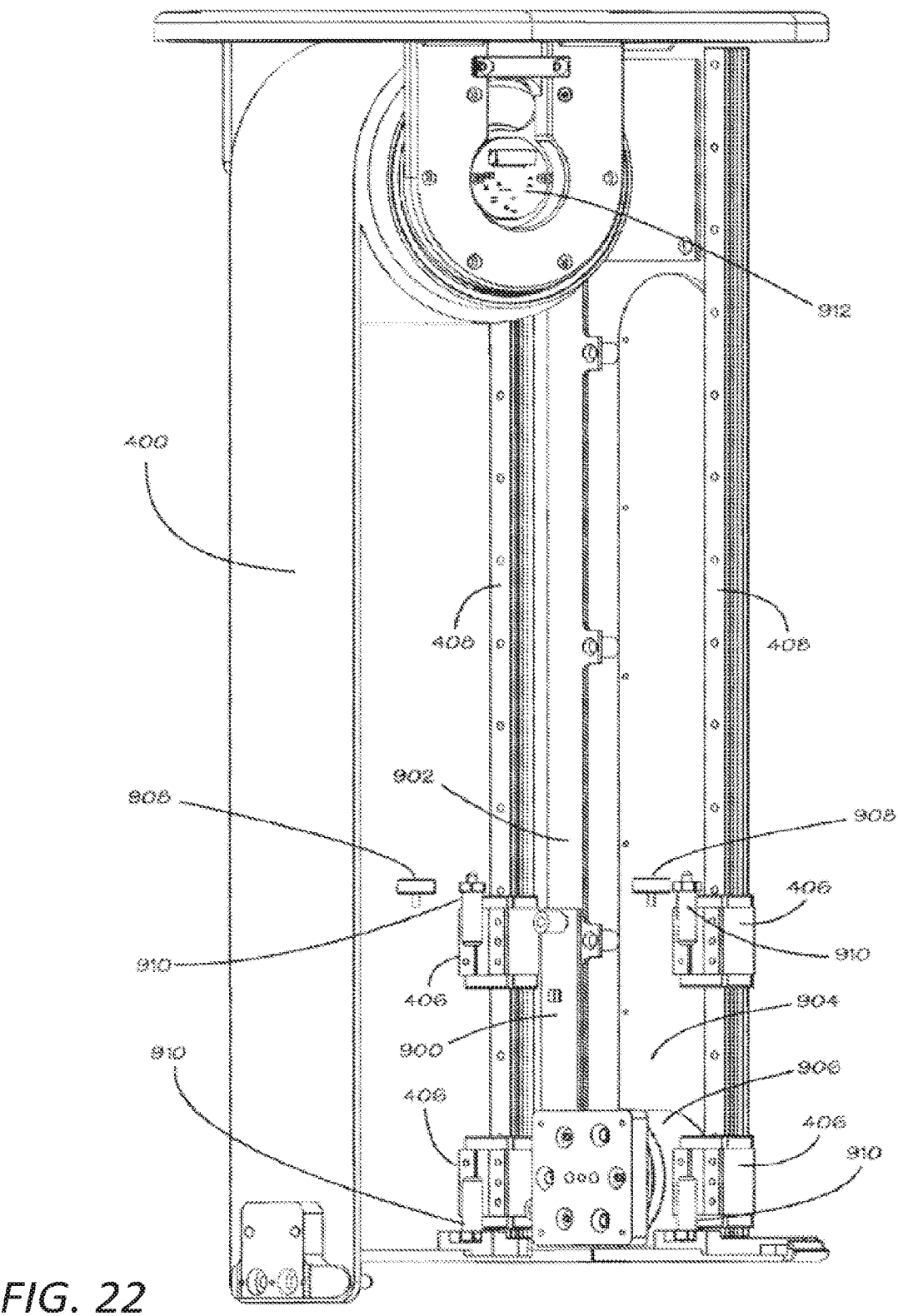
FIG. 22 is a perspective view of a constant force spring assembly with additional components of the setup joint.

FIG. 22 is a perspective view of the constant force spring 400 shown in FIG. 19 with additional components shown. As previously discussed, the vertical column 300 may be supported by a track 408 and carriage 406 assembly. A brake may be provided to hold the vertical column in a fixed position so that no power is required when the position of the vertical column is not being changed. The brake may be in the form of a brake that clamps the extended portion of the constant force spring in a fixed position, a brake that prevents the drum from rotating, or a brake that prevents the vertical column from moving, such as the magnetic brake illustrated that magnetically grips an armature 904 with a magnetic brake shoe 906.

The motor includes a primary sensor 912, which is a rotary sensor that provides an absolute rotary position for the motor. One part of the primary sensor is mounted on the motor rotor. The other part of the primary sensor is mounted to a mechanical ground, such as the motor stator. The primary sensor is coupled to a control module that provides controlled electrical current to the motor to provide the desired motion and torque from the motor. The primary sensor is used for motor commutation and shaft speed control.

A secondary sensor 900, 902 may be provided to provide data for the position of the vertical column to the control module. The secondary sensor 900, 902 may be mounted to the carriage that supports the vertical column and to a mechanical ground such as the frame that supports the stationary rails 408 on which the carriage slides. The secondary sensor 900, 902 provides an absolute linear position.

The secondary sensor 900, 902 provides a backup to the primary sensor 912. Readings from the two sensors may be compared to confirm that the vertical column as sensed by the secondary sensor 900, 902 is moving as expected based on the rotation of the motor as sensed by the primary sensor 912.

The secondary absolute position sensor 900, 902 may be used to periodically calibrate the force required to compensate for irregularities in the force provided by the constant force spring 400. The calibration routine uses the secondary sensor 900, 902 in conjunction with the motor and the primary motor sensor 912. Because the effective radius of the constant force spring 400 is a function of how much is payed out, the ratio between the primary and secondary sensors is variable. This variable ratio is taken into consideration in the calibration. Such calibration will generally be needed infrequently.

Instruments supported by the vertical column may be provided with machine readable identification that enables the control module to determine the amount of weight added to the vertical column by the instrument. The machine readable identification may provide a general weight for the type of instrument or a specific weight for the individual instrument, either directly or by reference to a database of instrument information. The control module is able to adjust the electrical current provided to the motor to provide the desired force from the motor to compensate for the weight of the installed surgical instrument.

The track 408 and carriage 406 assembly includes mechanical stops to prevent the carriages from running off the tracks. The mechanical stops may include rubber bumpers 908 that limit the carriage motion with only a small amount of material deformation, perhaps 1 to 1.5 mm. The mechanical stops may also include spring stops 910 that limit the carriage motion while providing a greater amount of yield, perhaps 3 to 3.5 mm. It will be appreciated that even the spring stops 910 may stop the carriage somewhat abruptly.

In some embodiments, the control module may use the motor to resist movement toward the end of the range of travel and bring the carriage 406 to a stop over a greater distance to avoid abruptly stopping the movement of the carriage 406. The control software implemented stop may gradually increase the force required to move the carriage assembly over the end of the range of carriage travel, perhaps over the final 12 to 20 mm of carriage travel. The increase in force provided by the motor to resist motion through the end of the range of travel for the carriage 406 may be applied non-linearly to stop the carriage 406 with a desired deceleration profile. The software implemented stop may provide a force that gradually increases from a zero force at the beginning of the range, something may be difficult to implement with a mechanical stop.

As discussed above, it may be desirable to provide some low compliance movement at the ends of the range of motion of the carriage 406 during operating table motion. In addition to the reasons discussed above, if the carriage 406 is at the end of its range of motion, operating table motion may not be possible. If the carriage 406 reaches a mechanical stop 908, 910 during operating table motion, the ability to move the operating table further is eliminated. Accordingly, the spring plunger 910 may be configured to push the carriage 406 off the limit of the mechanical stops 908, 910 to bring the carriage to rest at a position that allows for low compliance movement of the carriage in both directions. While joint 210 may include mechanical brakes or a drive system configured to hold the carriage in a fixed position when applied (so as to limit inadvertent movement of the joint or the like), control systems may be provided that regulate driving or braking by the drive or brake system when the spring plungers 910 are depressed and/or when the joint 210 is moved within a software defined threshold proximity to a physical range of motion limit (e.g., moved within a range of motion limit envelope extending from the physical range of motion limit).

FIGS. 23A-23D illustrate an exemplary simplified system diagrams illustrating various joint configurations where the joint 500 is at different positions along its range of motion 501 relative to one of its physical range of motion limits 502. The opposite end of the range of motion 501 has been omitted in the illustration and following description for the purposes of simplification and clarity. It should be understood that the FIGS. 23A-23D illustrate one end of the range of motion 501 of the joint 500 and that the configurations and control algorithms described below may be similarly implemented at the opposite range of motion limit of joint 500.

The joint 500 may be any joint along the kinematic linkage supporting a manipulator such as a set-up joint linkage. The joint 500 may also have a drive or brake system associated with the joint 500 that when applied hold the carriage in a fixed position. The driving or braking by the drive or brake system may be selectively applied and released by a user through a user input (e.g., selectively releasing a clutch or the like). When a user is manually moving joint 500 through its range of motion 501, a surgical system computing unit may implement a number of different control algorithms in response to and depending on a position of the joint 500 relative to a physical range of motion limit 502 and/or a threshold duration of time in which the joint 500 is moved to or positioned within various proximity thresholds as will be described in more detail below.

Figure 23B:
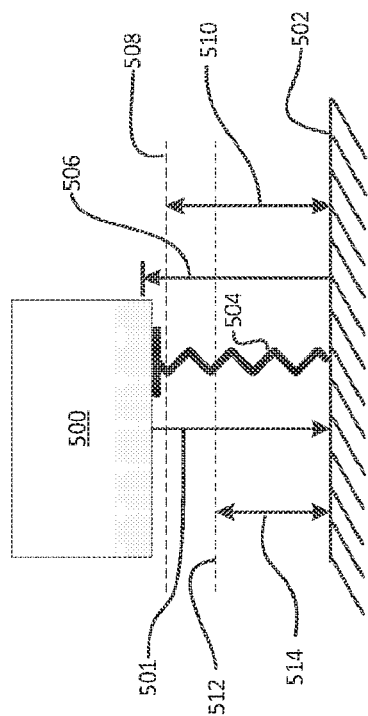
FIGS. 23A-23D illustrate exemplary simplified system diagrams illustrating various joint configurations where the joint is at different positions along its range of motion relative to one of its physical range of motion limits.
Figure 23D:
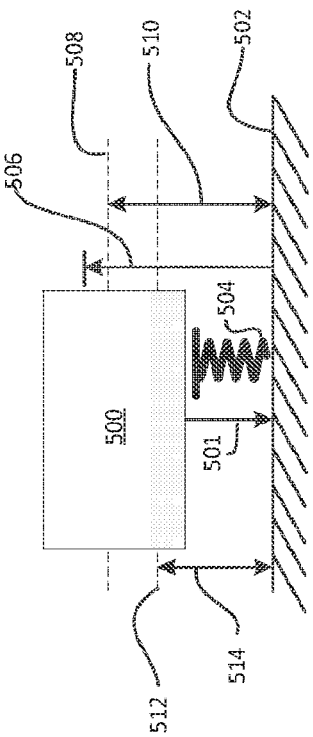
Figure 23A:
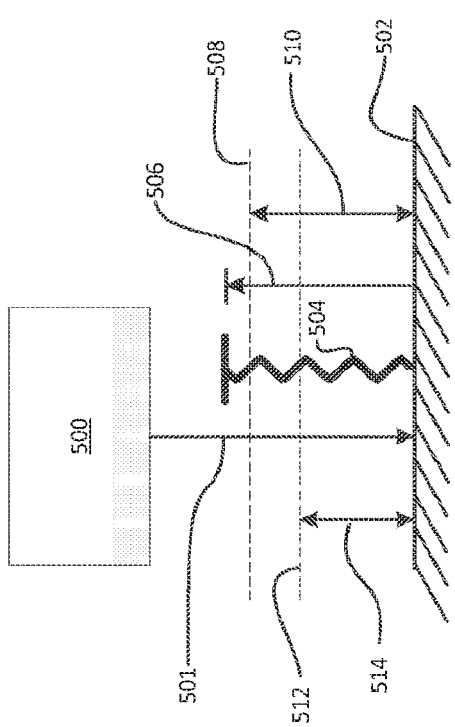

As illustrated in FIGS. 23A-23D, a spring 504 may be positioned at the physical range of motion limit 502 and may define a push out zone 506. Spring 504 may be a single spring or may represent a plurality of springs (physical, mechanical, tunable and/or virtual). The push out zone 506 may define a range where the spring 504 absorbs and counters movement of the joint 500 toward the physical range of motion limit 502. In FIG. 23A the joint 500 is illustrated outside the push out zone 506 with the spring 504 fully extended and FIG. 23B illustrates the joint 500 moved to and positioned within the push out zone 506 where the spring 504 is slightly compressed and acting on joint 500.

A first threshold 508 may be spaced apart a distance from the physical range of motion limit 502. The first threshold 508 may be a software defined range of motion limit that delineates a range of motion limit envelope 510 that extends between the physical range of motion limit 502 and the threshold 508. The software defined range of motion limit 508 may describe a preferred minimum spacing of the joint 500 from a physical range of motion limit 502. In some embodiments, the envelope 510 may extend 1 inch or less from the physical range of motion limit 502, preferably 0.5 inches or less (e.g., about 0.25 inches or the like). In some embodiments, the first threshold 508 may be defined distal to a push out zone 506 associated with the spring 504 (e.g., at a location between the end of the push out zone 506 and the physical range of motion limit 502). A computing unit coupled with a drive or brake system associated with the joint 500 may delay an application of a driving or braking by the drive or brake system when the joint 500 is moved past this threshold 508 and positioned within the range of motion limit envelope 510. The delay in the application of the driving or braking by the drive or brake system may allow the spring 504 time to push the joint 500 from the range of motion envelope 510 prior to reapplication of the driving or braking by a drive or brake system to fix a position of the joint 500.

Figure 23C:
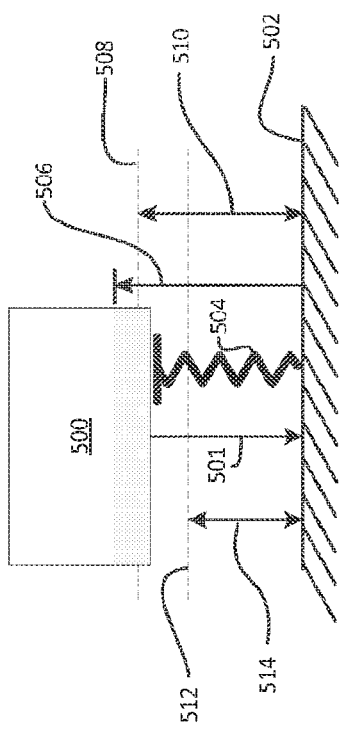

For example, FIG. 23C illustrates joint 500 moved past threshold 508 and positioned within the range of motion limit envelope 510. If a user releases a clutch button associated with the drive or brake system or otherwise signals for a reapplication of the driving or the braking while the joint 500 is positioned within the range of motion limit envelope 510, a computing unit of the system may not immediately reapply the driving or the braking in response to the user input as it may be undesirable to have the joint 500 fixed at a position with close proximity to its physical range of motion limit 502. Accordingly, the computing unit may delay an application of the driving or braking by the drive or brake system which may allow the spring 504 to push the joint 500 away from the physical range of motion limit 502. When the computing unit detects that the joint 500 has been pushed out from the range of motion limit envelope 510 (e.g., to a position as illustrated for example in FIG. 23B) by the spring 504 or by the user, the computing unit may then allow for or automatically trigger a reapplication of the driving or braking by the drive or brake system of the joint 500 to fix the joint 500 at a position preferably spaced from the physical range of motion limit 502.

In some embodiments, the computing unit of the system may delay reapplication of the driving or braking for 1-10 seconds, preferably between 3-8 seconds or about 5 seconds. If the spring 504 push out force is being countered by other external forces (e.g., a user maintaining a pressure toward the range of motion limit 502 after releasing the clutch or otherwise signaling for reapplication of a driving or brake signal, or the like), the computing unit may reapply the driving or braking by the drive or brake system after the delay duration to fix the joint 500 at a position within the range of limit envelope 510 (e.g., as illustrated in FIG. 23C and FIG. 23D). Thereafter, the computing unit may be configured to output an error signal to the user to indicate the undesirable configuration of joint 500. The error signal may be outputted in an audio, visual, and/or haptic manner. Optionally, light indicators on the system may flash, an error may be output to a display associated with the system, an error buzz or voice describing the error may be outputted from a speaker, or a vibration generator associated with the joint may be activated such that a user may feel and receive feedback indicative of the undesirable configuration.

Thereafter, to clear the error, the user may actuate the clutch and physically move the joint 500 away from the range of motion limit 502, or in some embodiments, may quickly actuate the clutch (in a quick on/off or "burping" fashion) to signal a brief release the driving or the braking by the drive or brake system. Although the signal is for a brief release of the driving or braking (and for immediate reapplication of the driving or braking), the computing unit may delay the reapplication of the driving or braking in a manner similar to that described above as it detects the position of the joint 500 within the range of motion envelope 510. This delay in reapplication may allow the spring 504 to automatically push the joint 500 out of the range of motion limit envelope 510 (if there are no external forces overcoming the spring force). The control system may then detect movement of the joint 500 outside threshold 508 and the driving or braking may be automatically reapplied after the joint 500 is pushed from the range of motion limit envelope 510 (e.g., FIG. 23B). Once the joint 500 is returned to a position in a preferred range of motion of the joint 500, the computing unit may clear the error signal. In many embodiments, the automatic push out control may provide a more intuitive and desirable user interface.

A second threshold 512 may also be a software defined threshold that delineates a range of motion envelope 514 where movement of the joint 500 past this threshold 512 and positioning the joint 500 within the envelope 514 may trigger LHBN movement mode. As discussed above, in some embodiments, the joint 500 must resides within the envelope 514 for a threshold duration of time before entering the movement mode. While not necessary, in some embodiments, the threshold 512 is distal to threshold 508. Accordingly, range of motion envelope 510 may encompass range of motion envelope 514. Thus if the user releases the port clutch or otherwise signals for reapplication of a driving or a braking while the joint 500 is positioned within envelope 514 and prior to entering the movement mode, the computing unit may delay reapplication so as to allow the spring 504 to push the joint 500 out from the physical range of motion limit 502 and to a position outside of envelope 510 prior to allowing or triggering reapplication of the driving or braking by the drive or brake system. As discussed above, the joint may include one or more sensors (e.g., sensors 900, 902) to provide data for the position of the joint to the control module. The sensors may be configured to provide an absolute linear position. In some embodiments, the sensors may be rotary encoders or shaft encoders for detecting angles of the motor shaft which may then be used to identify a position of the joint.

While illustrated as a vertical prismatic joint (e.g., where the range of motion limit is associated with a full vertical compression or a full vertical extension of the joint), it should be understood that the configurations and control algorithms described above are also applicable to other prismatic joints (e.g., horizontal prismatic joints) along the kinematic linkage supporting the manipulator (e.g., other set-up joints and/or set-up structure linkages). Additionally, the above configurations and control algorithms may be applicable to cylindrical joints with corresponding thresholds defined by rotational degrees of freedom.

Spring 504 may be a physical spring (e.g., springs 910). In some embodiments, it may be preferable to utilized mechanical springs. The use of mechanically springs may be advantageous in some embodiments as no servo motor is required—passive dynamics may be sufficient. Optionally, the spring 504 may be a virtual spring (e.g., through software control of a servo) that mimics a physical spring installed at the range of motion limit. In some embodiments, a combination of physical and virtual springs may be used for the automatic push out function.

For example, in the exemplary embodiment illustrated in FIGS. 16-22, the mechanical constant force spring is coupled with a motor. The motor may tune the constant force spring by increasing or decreasing the spring constant as desired. During operation, the constant force spring may provide a counterbalance for the system that is adjustable depending on the types of instruments attached. For example, if a heavier instrument is installed, the motor may be controlled to increase the spring constant of the constant force spring to act as a counterbalance. While the constant force spring may be used for counter balancing purposes, the constant force spring may also be used for the push out function. For example, the motor may be driven to increase or decrease a spring constant depending on a position of the joint (e.g., joint 500). For example, when the joint is near a range of motion limit (e.g., within envelope 510 extending from limit 502), the motor may be driven to increase the spring constant of the constant force spring to provide a force which pushes the joint away from the range of motion limit 502. Thus, in some embodiments a combination of passive springs, active springs (e.g., spring 400), and virtual springs may be used to absorb and counter movement of the joint 500 toward a range of motion limit 502 and may provide the push out force to push the joint 500 away from the range of motion limit to a more preferable position prior to engaging a driving or braking by the drive or brake system.

In further aspects, a safety control algorithm may be provided. The system may be configured to detect inadvertent motion of the joint 500 beyond a software defined range of motion limit 508 (e.g., the joint 500 is moving within the range of motion limit envelope 510). When the system detects such a motion while the driving or braking by the drive or brake system is being applied, the system may be configured to release the driving or braking to allow the excess motion to be absorbed and counteracted by the spring 504. Such a safety feature may reduce forces inadvertently exerted against objects or patients by linkages distal to the joint.

In a system with redundant degrees of freedom, if a relatively more distal joint is at a range of motion limit and one or more relatively proximal joints are moved in a degree of freedom redundant to the distal joint, the arm distal of the distal joint may inadvertently exert an extremely high force against an object. For example, if a prismatic vertical set-up joint (e.g., joint 106) is fully compressed, and then a column (e.g., column 88) is lowered, there may not be available range of motion in the vertical set-up joint, and the manipulator or instrument may exert the entire force of the lowering boom.

Accordingly, the system may be configured to detect inadvertent movement of the joint 500 beyond a software defined range of motion limit 508. In response the system may release the joint brakes to allow for an additional buffer zone or end of range motion where springs (e.g., springs 910) and/or bumpers (e.g., bumpers 908) may absorb and counteract the excess motion such that arms distal to the joint 500 will exert less force against the object. Additionally, in some embodiments, when the drive or brake system is released and the joint is pushed into range of motion limit envelope 510, a constant force spring 400 may also act on the joint 500 in a push out manner to absorb the inadvertent forces. The springs and bumpers may provide a compliant buffer, reducing the force applied to an object or patient by joints, linkages, or instruments distal to the joint 500.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A teleoperated system comprising:
   a kinematic structure having a joint;
   a drive or brake system for controlling the joint; and
   a computing unit coupled with the drive or brake system, the computing unit configured to:
      detect that the joint is between a software defined range of motion limit for the joint and a physical range of motion limit for the joint, the software defined range of motion limit being spaced a distance apart from the physical range of motion limit; and
      delay for a duration of time, in response to detecting the joint between the software defined range of motion limit and the physical range of motion limit, applying the drive or brake system to stop motion of the joint.

2. The teleoperated system of claim 1, further comprising:
   a switch configured for operator actuation to selectively drive or brake with the drive or brake system and allow for manual positioning of the kinematic structure.

3. The teleoperated system of claim 1, wherein the computing unit is further configured to, in response to a joint operation, selectively drive or brake with the drive or brake system to allow for manual positioning of the kinematic structure.

4. The teleoperated system of claim 1, wherein:
   the joint comprises a prismatic joint; and
   the physical range of motion limit is encountered when the prismatic joint is fully extended or when the prismatic joint is fully compressed.

5. The teleoperated system of claim 1, wherein the joint includes one or more springs at the physical range of motion limit, wherein the one or more springs are configured to resist movement of the joint to the physical range of motion limit.

6. The teleoperated system of claim 5, wherein the one or more springs comprise one or more virtual springs.

7. The teleoperated system of claim 5, wherein the one or more springs are configured to push the joint to a position farther from the physical range of motion limit than the distance.

8. The teleoperated system of claim 1, wherein the computing unit is further configured to apply, with the drive or brake system, a resistance force that increases as the joint gets nearer to the physical range of motion limit.

9. The teleoperated system of claim 1, wherein the computing unit is further configured to output an error signal in a manner perceptible to an operator when the drive or brake system is applied with the joint positioned between the physical range of motion limit and the software defined range of motion limit.

10. The teleoperated system of claim 9, wherein the computing unit is further configured to clear the error signal after the joint is moved to a position farther from the physical range of motion limit than the distance.

11. The teleoperated system of claim 1, wherein the teleoperated system is a telesurgical system, and wherein the kinematic structure comprises a manipulator arm.

12. The teleoperated system of claim 1, wherein the drive or brake system comprises a brake system.

13. A method of controlling a teleoperated system, the method comprising:
   detecting, by a computing unit, that a joint of a kinematic structure of the teleoperated system is between a software defined range of motion limit for the joint and a physical range of motion limit for the joint, the software defined range of motion limit being spaced a distance apart from the physical range of motion limit; and
   delaying for a duration of time, by the computing unit in response to the detecting, application of a drive or brake system to stop motion of the joint.

14. The method of claim 13, further comprising, in response to a joint operation, selectively driving or braking with the drive or brake system to allow for manual positioning of the kinematic structure.

15. The method of claim 13, further comprising: resisting movement of the joint to the physical range of motion limit using one or more springs at the physical range of motion limit.

16. The method of claim 15, wherein the one or more springs are one or more virtual springs.

17. The method of claim 13, further comprising applying, with the drive or brake system, a resistance force that increases as the joint gets nearer to the physical range of motion limit.

18. The method of claim 13, further comprising:
   outputting an error signal in a manner perceptible to an operator when the drive or brake system is applied with the joint positioned between the physical range of motion limit and the software defined range of motion limit; and
   clearing the error signal after the joint is moved to a position farther from the physical range of motion limit than the distance.

19. A non-transitory machine-readable medium comprising a plurality of machine-readable instructions which when executed by one or more processors associated with a teleoperated system are adapted to cause the one or more processors to perform a method comprising:

detecting, by a computing unit, that a joint of a kinematic structure of the teleoperated system is between a software defined range of motion limit for the joint and a physical range of motion limit for the joint, the software defined range of motion limit being spaced a distance apart from the physical range of motion limit; and delaying for a duration of time, by the computing unit in response to the detecting, application of a drive or brake system to stop motion of the joint.

20. The non-transitory machine-readable medium of claim 19, the method further comprising:

applying, with the drive or brake system, a resistance force that increases as the joint gets nearer to the physical range of motion limit; and resisting movement of the joint to the physical range of motion limit using one or more virtual springs associated with the physical range of motion limit.

* * * * *

UNITED STATES PATENT AND TRADEMARK OFFICE
CERTIFICATE OF CORRECTION

PATENT NO. : 10,779,899 B2  
APPLICATION NO. : 16/016436  
DATED : September 22, 2020  
INVENTOR(S) : Paul G. Griffiths et al.

Page 1 of 1

It is certified that error appears in the above-identified patent and that said Letters Patent is hereby corrected as shown below:

On the Title Page

(63) Related U.S. Application Data:
Please delete "Continuation of application No. 15/126,541, filed as application No. PCT/US2015/021074 on Mar. 17, 2015, now Pat. No. 10,028,793." and insert --Continuation of application No. 15/126,541, filed on Sep. 15, 2016, now Pat. No. 10,028,793, which is a 371 of application No. PCT/US2015/021074, filed on Mar. 17, 2015.--.

Signed and Sealed this  
Twenty-seventh Day of October, 2020

Andrei Iancu  
*Director of the United States Patent and Trademark Office*